US010154918B2

(12) United States Patent
Haselby et al.

(10) Patent No.: US 10,154,918 B2
(45) Date of Patent: Dec. 18, 2018

(54) ENDOLUMINAL PROSTHESIS WITH FIBER MATRIX

(71) Applicant: Cook Medical Technologies LLC, Bloomington, IN (US)

(72) Inventors: Kenneth A. Haselby, Battle Ground, MI (US); William J. Havel, West Lafayette, IN (US); Rick Hadley, Otterbein, IN (US); Keith R. Milner, West Lafayette, IN (US); Blayne A. Roeder, Bloomington, IN (US); Sara M. Sherman, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 684 days.

(21) Appl. No.: 14/136,677

(22) Filed: Dec. 20, 2013

(65) Prior Publication Data

US 2014/0188212 A1 Jul. 3, 2014

Related U.S. Application Data

(60) Provisional application No. 61/747,173, filed on Dec. 28, 2012.

(51) Int. Cl.
*A61F 2/06* (2013.01)
*A61F 2/90* (2013.01)
(Continued)

(52) U.S. Cl.
CPC .................. *A61F 2/90* (2013.01); *A61F 2/07* (2013.01); *D01D 5/003* (2013.01); *D01D 5/0084* (2013.01);
(Continued)

(58) Field of Classification Search
CPC ...... A61F 2/07; A61F 2/06; A61F 2/90; A61F 2/915; A61F 2/89; A61F 2/82; A61F 2/91;
(Continued)

(56) References Cited

U.S. PATENT DOCUMENTS 3,280,229 A 10/1966 Simons
4,130,904 A 12/1978 Whalen
(Continued)

FOREIGN PATENT DOCUMENTS

EP 2708208 A2 3/2014
JP 2004-313320 A 11/2004
(Continued)

OTHER PUBLICATIONS

The Free Dictionary, Definition of Transverse, accessed on Feb. 23, 2017, <http://www.thefreedictionary.com/transverse>.*
(Continued)

*Primary Examiner* — Robert Lynch
*Assistant Examiner* — Mohamed Gabr
(74) *Attorney, Agent, or Firm* — Brinks Gilson & Lione

(57) ABSTRACT

An expandable endoluminal prosthesis may include a graft body and a support structure attached to the graft body. The graft body may include a tubular body of nonwoven electrospun fibers disposed about a longitudinal axis. A first fiber matrix segment may be attached to and extend in a transverse direction along the tubular body. A second fiber matrix segment may be attached to and extend in a longitudinal direction along the tubular body.

17 Claims, 10 Drawing Sheets

(51) Int. Cl.
*A61F 2/07* (2013.01)
*D01D 5/00* (2006.01)

(52) U.S. Cl.
CPC . *A61F 2002/072* (2013.01); *A61F 2210/0076* (2013.01); *A61F 2250/0028* (2013.01)

(58) Field of Classification Search
CPC .................. A61F 2/86; A61F 2002/072; A61F 2002/075; Y10T 442/614; Y10T 428/2913
USPC ............ 623/1.15, 1.13, 1.39, 1.1, 1.44, 23.7
See application file for complete search history.

(56) References Cited

U.S. PATENT DOCUMENTS

| | | | |
|---|---|---|---|
| 4,323,525 A | 4/1982 | Bornat | |
| 4,434,797 A | 3/1984 | Silander | |
| 4,629,458 A | 12/1986 | Pinchuk | |
| 4,657,544 A | 4/1987 | Pinchuk | |
| 4,689,186 A | 8/1987 | Bornat | |
| 4,759,757 A | 7/1988 | Pinchuk | |
| 4,776,337 A | 10/1988 | Palmaz | |
| 5,078,736 A | 1/1992 | Behl | |
| 5,628,788 A | 5/1997 | Pinchuk | |
| 5,693,085 A | 12/1997 | Buirge et al. | |
| 5,716,395 A | 2/1998 | Myers et al. | |
| 5,728,150 A | 3/1998 | McDonald et al. | |
| 5,755,774 A | 5/1998 | Pinchuk | |
| 5,769,884 A | 6/1998 | Solovay | |
| 5,866,217 A | 2/1999 | Stenoien et al. | |
| 6,007,573 A | 12/1999 | Wallace et al. | |
| 6,110,198 A | 8/2000 | Fogarty et al. | |
| 6,306,424 B1 | 10/2001 | Vyakarnam et al. | |
| 6,334,868 B1 | 1/2002 | Ham | |
| 6,398,803 B1 | 6/2002 | Layne et al. | |
| 6,537,310 B1 | 3/2003 | Palmaz et al. | |
| 6,558,414 B2 | 5/2003 | Layne | |
| 6,579,314 B1 | 6/2003 | Lombardi et al. | |
| 6,616,435 B2 | 9/2003 | Lee et al. | |
| 6,638,621 B2 | 10/2003 | Anderson | |
| 6,685,956 B2 | 2/2004 | Chu et al. | |
| 6,753,311 B2 | 6/2004 | Fertala et al. | |
| 6,770,087 B2 | 8/2004 | Layne et al. | |
| 6,790,455 B2 | 9/2004 | Chu et al. | |
| 6,821,479 B1 | 11/2004 | Smith et al. | |
| 6,858,168 B1 | 2/2005 | Vollrath et al. | |
| 6,865,810 B2 | 3/2005 | Stinson | |
| 6,936,298 B2 | 8/2005 | Chaikof et al. | |
| 6,989,195 B2 | 1/2006 | Anderson | |
| 7,070,836 B2 | 7/2006 | Czado | |
| 7,081,622 B2 | 7/2006 | Kameoka et al. | |
| 7,105,229 B2 | 9/2006 | Anderson | |
| 7,105,810 B2 | 9/2006 | Kameoka et al. | |
| 7,112,417 B2 | 9/2006 | Vyakarnam et al. | |
| 7,134,857 B2 | 11/2006 | Andrady et al. | |
| 7,143,963 B2 | 12/2006 | Tani et al. | |
| 7,172,765 B2 | 2/2007 | Chu et al. | |
| 7,244,272 B2 | 7/2007 | Dubson et al. | |
| 7,247,338 B2 | 7/2007 | Pui et al. | |
| 7,306,756 B2 | 12/2007 | Edwin et al. | |
| 7,390,524 B1 | 6/2008 | Chen | |
| 7,413,575 B2 | 8/2008 | Phaneuf et al. | |
| 7,591,841 B2 | 9/2009 | Hossainy et al. | |
| 7,704,274 B2 | 4/2010 | Boyle et al. | |
| 7,736,687 B2 | 6/2010 | Sims et al. | |
| 7,794,833 B2 | 9/2010 | Balkus, Jr. et al. | |
| 7,799,261 B2 | 9/2010 | Orr et al. | |
| 7,815,763 B2 | 10/2010 | Fierens et al. | |
| 7,824,601 B1 | 11/2010 | Stankus et al. | |
| 7,854,760 B2 | 12/2010 | Molaei et al. | |
| 7,922,761 B2 | 4/2011 | Shalev et al. | |
| 7,947,069 B2 | 5/2011 | Sanders | |
| 8,057,535 B2 | 11/2011 | Hashi et al. | |
| 8,100,683 B2 | 1/2012 | Orr et al. | |
| 8,123,794 B2 | 2/2012 | Flagle et al. | |
| 8,157,857 B2 | 4/2012 | Case et al. | |
| 8,178,030 B2 | 5/2012 | Anneaux et al. | |
| 8,257,640 B2 | 9/2012 | Anneaux et al. | |
| 8,262,979 B2 | 9/2012 | Anneaux et al. | |
| 2001/0047198 A1 | 11/2001 | Drasler et al. | |
| 2002/0045931 A1 | 4/2002 | Sogard et al. | |
| 2003/0100944 A1 | 5/2003 | Laksin et al. | |
| 2003/0109917 A1 | 6/2003 | Rudin et al. | |
| 2003/0195611 A1 | 10/2003 | Greenhalgh et al. | |
| 2003/0211135 A1 | 11/2003 | Greenhalgh et al. | |
| 2004/0018226 A1 | 1/2004 | Wnek et al. | |
| 2004/0030377 A1 | 2/2004 | Dubson et al. | |
| 2004/0037813 A1 | 2/2004 | Simpson et al. | |
| 2004/0051201 A1 | 3/2004 | Greenhalgh et al. | |
| 2004/0116997 A1 | 6/2004 | Taylor et al. | |
| 2004/0199241 A1 | 10/2004 | Gravett et al. | |
| 2004/0241436 A1 | 12/2004 | Hsieh et al. | |
| 2005/0064168 A1 | 3/2005 | Dvorsky et al. | |
| 2005/0104258 A1 | 5/2005 | Lennhoff | |
| 2005/0137675 A1* | 6/2005 | Dubson ...................... | A61F 2/06 623/1.4 |
| 2005/0137680 A1 | 6/2005 | Ortiz et al. | |
| 2005/0273155 A1* | 12/2005 | Bahler ...................... | A61F 2/07 623/1.13 |
| 2006/0048355 A1 | 3/2006 | Kim | |
| 2006/0085063 A1 | 4/2006 | Shastri et al. | |
| 2006/0195142 A1 | 8/2006 | Shalaby | |
| 2006/0200232 A1 | 9/2006 | Phaneuf et al. | |
| 2006/0213829 A1 | 9/2006 | Rutledge et al. | |
| 2006/0259131 A1 | 11/2006 | Molaei et al. | |
| 2006/0264140 A1 | 11/2006 | Andrady et al. | |
| 2007/0031607 A1 | 2/2007 | Dubson et al. | |
| 2007/0043428 A1 | 2/2007 | Jennings et al. | |
| 2007/0087027 A1 | 4/2007 | Greenhalgh et al. | |
| 2007/0142896 A1* | 6/2007 | Anderson .................. | A61F 2/07 623/1.13 |
| 2007/0162110 A1 | 7/2007 | Dave | |
| 2007/0198077 A1* | 8/2007 | Cully ...................... | A61B 17/11 623/1.12 |
| 2008/0027531 A1 | 1/2008 | Reneker et al. | |
| 2008/0200975 A1 | 8/2008 | Dubson | |
| 2008/0208325 A1 | 8/2008 | Helmus et al. | |
| 2008/0241352 A1 | 10/2008 | Shalaby | |
| 2009/0069904 A1 | 3/2009 | Picha | |
| 2009/0088828 A1* | 4/2009 | Shalev ...................... | A61F 2/06 623/1.2 |
| 2009/0112306 A1 | 4/2009 | Bonsignore et al. | |
| 2009/0132022 A1 | 5/2009 | Banas | |
| 2009/0138070 A1 | 5/2009 | Holzer et al. | |
| 2009/0227026 A1 | 9/2009 | Rapoport et al. | |
| 2009/0248131 A1 | 10/2009 | Greenan | |
| 2010/0179644 A1 | 7/2010 | Jennings et al. | |
| 2010/0222771 A1 | 9/2010 | Mitchell et al. | |
| 2010/0241214 A1 | 9/2010 | Holzer et al. | |
| 2010/0318193 A1 | 12/2010 | Desai et al. | |
| 2011/0009949 A1 | 1/2011 | Stankus et al. | |
| 2011/0022149 A1 | 1/2011 | Cox et al. | |
| 2011/0022159 A1 | 1/2011 | Fierens et al. | |
| 2011/0135806 A1 | 6/2011 | Grewe et al. | |
| 2011/0262684 A1 | 10/2011 | Wintsch et al. | |
| 2011/0301696 A1 | 12/2011 | Mangiardi | |
| 2012/0141656 A1 | 6/2012 | Orr et al. | |
| 2012/0239134 A1* | 9/2012 | Dierking .................. | A61F 2/07 623/1.15 |
| 2013/0018220 A1 | 1/2013 | Vad et al. | |
| 2013/0122248 A1 | 5/2013 | Haselby et al. | |

FOREIGN PATENT DOCUMENTS

| | | |
|---|---|---|
| JP | 2006-283241 | 10/2006 |
| JP | 2006-283241 A | 10/2006 |
| JP | 2007-303021 | 11/2007 |
| WO | WO 96/35577 | 11/1996 |
| WO | WO 02/49536 A2 | 6/2002 |
| WO | WO 03/072287 A1 | 9/2003 |
| WO | WO 2009/002827 A2 | 12/2008 |

(56) References Cited

FOREIGN PATENT DOCUMENTS

| WO | WO 2010/112564 A1 | 10/2010 | | |
|----|-------------------|---------|---|---|
| WO | WO 2011082295 A2 | * | 7/2011 | ............... A61F 2/06 |
| WO | WO 2012/006072 A2 | 1/2012 | | |

OTHER PUBLICATIONS

Dictionary.com, Definition of About, acessed on Feb. 23, 2017, <http://www.dictionary.com/browse/about?>.*
Extended International Search Report for European Patent Application No. 13199440 dated Apr. 28, 2014 (6 pages).
European Patent Office Communication for EP 12192656.2 dated Aug. 6, 2014 (4 pages).
Salim et al., "Selective Nanofiber Deposition Via Electrodynamic Focusing", Nanotechnology, vol. 19, 2008, pp. 1-8.
Examination report for European Application No. 13199440.2 dated Dec. 6, 2016, 3 pages.

* cited by examiner

ENDOLUMINAL PROSTHESIS WITH FIBER MATRIX

RELATED APPLICATION

The present application claims priority to U.S. Provisional Application Ser. No. 61/747,173 filed on Dec. 28, 2012, the contents of which application is herein incorporated by reference in its entirety.

TECHNICAL FIELD

This disclosure relates to endoluminal medical devices for implantation within the human or animal body for treatment of endovascular disease. More particularly, it relates to a graft material for an endoluminal prosthesis, an endoluminal prosthesis having a graft material, and methods of manufacturing a graft material.

BACKGROUND

Covered stents, or stent grafts, have been used to treat a variety of medical conditions, including aneurysms, occluded vessels, and restenosis. For example, an aneurysm may occur in a blood vessel in a location where, due to age, disease, or genetic predisposition, the blood vessel strength or resiliency is insufficient to enable the blood vessel wall to retain its shape as blood flows therethrough. This may result in ballooning or stretching of the blood vessel at the location having limited strength or resiliency, thereby forming an aneurysmal sac. If the aneurysm is left untreated, the blood vessel wall may continue to expand to the point where the remaining strength of the blood vessel wall is insufficient to prevent rupture. In this instance, the blood vessel may fail at the location of the aneurysm, often with fatal result.

To prevent rupture, a stent graft of a tubular construction may be introduced into the blood vessel, for example, intraluminally. Typically, the stent graft is deployed and secured in a location within the blood vessel such that the stent graft spans the aneurysmal sac. The outer surface of the stent graft, at its opposed ends, may be sealed to the interior wall of the blood vessel at locations where the blood vessel wall has not suffered a loss of strength or resiliency. Blood flow in the vessel may be channeled through the hollow interior of the stent graft, thereby reducing, or possibly eliminating, the stress on the blood vessel wall at the location of the aneurysmal sac. The graft material of the stent graft may be substantially nonporous so that blood may be prevented from leaking into the aneurysmal sac. This may reduce the risk of rupture of the blood vessel wall at the location of the aneurysmal sac while allowing blood to continue to flow through the stent graft to the downstream blood vessels without interruption.

Various materials and methods have been used to create coverings, or grafts, that may be applied to stents to form stent grafts. For example, grafts may be made using woven techniques, thin-sheet/tubing bonding, or other processes. Electrospinning may be used to form a suitable biocompatible coating or covering for a medical device, such as a stent graft. Electrospinning is a process for creating a nonwoven network of fibers using an electrically charged solution that is driven from a source to a target with an electrical field. More specifically, a solution is driven from an orifice, such as a needle. A voltage is applied to the orifice resulting in a charged solution jet or stream from the orifice to the target. The jet forms a conical shape, termed a Taylor cone, as it travels from the orifice. As the distance from the orifice increases, the cone becomes stretched until the jet splits or splays into many fibers prior to reaching the target. The fibers are extremely thin, typically in the nanometer range. The collection of fibers on the target forms a thin mesh layer of fibrous material.

SUMMARY

An expandable endoluminal prosthesis may include a graft body and a support structure attached to the graft body. The graft body may include a tubular body of nonwoven electrospun fibers disposed about a longitudinal axis. A first fiber matrix segment may be attached to the tubular body and extend in a transverse direction along the tubular body. A second fiber matrix segment may be attached to the tubular body and extend in a longitudinal direction along the tubular body.

In another example, an expandable endoluminal prosthesis may include a graft body and an expandable support structure attached to the graft body. The graft body may include a tubular body of nonwoven electrospun fibers disposed about a longitudinal axis. A transverse fiber matrix segment may be at least partially encapsulated within the tubular body and may extend in a transverse direction about the longitudinal axis. A longitudinal fiber matrix segment may be at least partially encapsulated within the tubular body and may extend in a primarily longitudinal direction. The support structure may be attached to at least one of the transverse fiber matrix segment and the longitudinal fiber matrix segment to attach the support structure to the graft body.

In another example, a method for preparing an endoluminal prosthesis may include providing an electrospinning apparatus including an orifice and a mandrel. An electric potential may be generated between the orifice and the mandrel. A first layer of nonwoven fibers may be formed on an outer surface of the mandrel by electrospinning a solution from the orifice onto the outer surface of the mandrel. A first fiber matrix segment may be positioned over the first layer of fibers. The first fiber matrix segment may extend in a transverse direction. A second fiber matrix segment may be positioned over the first layer of fibers. The second fiber matrix segment may extend in a longitudinal direction. An expandable support structure may be positioned over the first layer of fibers. A second layer of nonwoven fibers may be formed over the first fiber matrix segment, the second fiber matrix segment, and the support structure by electrospinning the solution from the orifice. Each of the first fiber matrix segment, the second fiber matrix segment, and the support structure may be at least partially encapsulated within a covering formed by the first layer of fibers and the second layer of fibers.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

The present disclosure relates to a graft material for an endoluminal prosthesis, an endoluminal prosthesis having a graft material, and methods of manufacturing a graft material.

In the present disclosure, the term "proximal" refers to a direction that is generally closest to the heart during a medical procedure, while the term "distal" refers to a direction that is farthest from the heart during a medical procedure.

Figure 1:
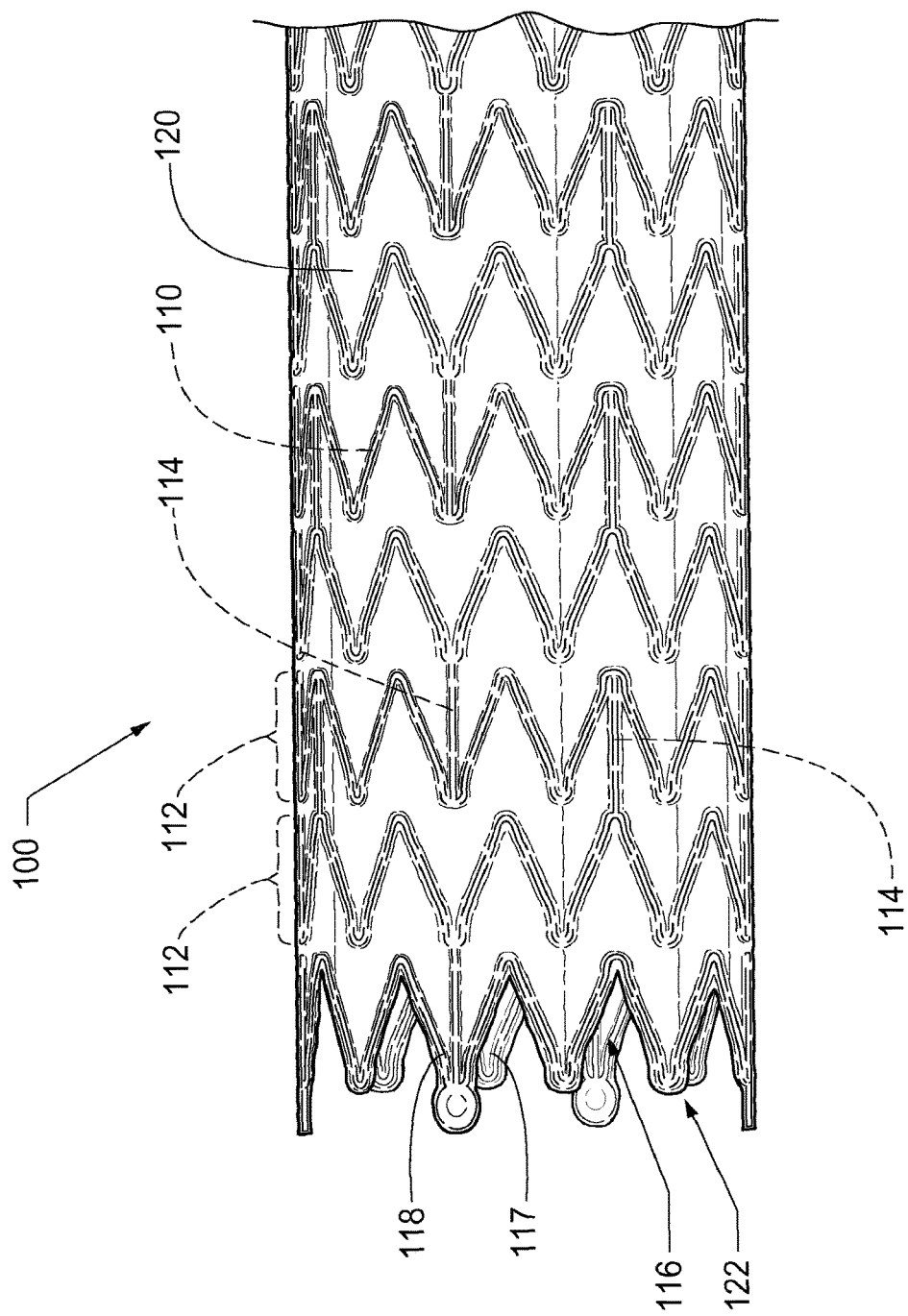
FIG. 1 illustrates one example of an endoluminal prosthesis.

FIG. 1 illustrates one example of an endoluminal prosthesis 100. In this example, the prosthesis 100 is a covered stent or a stent graft. The prosthesis 100 may include a support structure 110 (e.g., a stent) and a graft body 120 attached to the support structure. The support structure may have any configuration known in the art. For example, suitable support structures may include any of those described in U.S. Pat. No. 8,123,794 to Flagle et al. and U.S. Pat. No. 8,157,857 to Case et al., both of which are incorporated herein by reference. The support structure may be configured as a unitary structure or a plurality of separate structures which may collectively define the support structure. Additionally, or alternatively, the support structure may be made from a woven wire structure, a laser-cut cannula, individual interconnected rings, or another pattern or design. The support structure may be expandable (e.g., from a compressed delivery configuration to an expanded deployed configuration). For example, the support structure may be self-expandable, balloon-expandable, or may include self-expandable and balloon-expandable portions.

In one example, the support structure 110 may include a plurality of ring structures 112 interconnected by connector segments 114 as shown in FIG. 1. Each ring structure 112 may be a ring having an endless undulating pattern (e.g., a zig-zag pattern). The ring structure 112 may be formed by bending a wire into the desired pattern and joining the ends of the wire, by cutting the desired pattern from a solid tube of material, or by any other suitable method. The support structure 110 may be configured as a tubular member defined by the plurality of ring structures 112. For example, the ring structures 112 may be spaced from one another longitudinally along a length of the support structure. The connector segments 114 may extend longitudinally between adjacent ring structures 112 to maintain the spacing between the ring structures.

Figure 11:
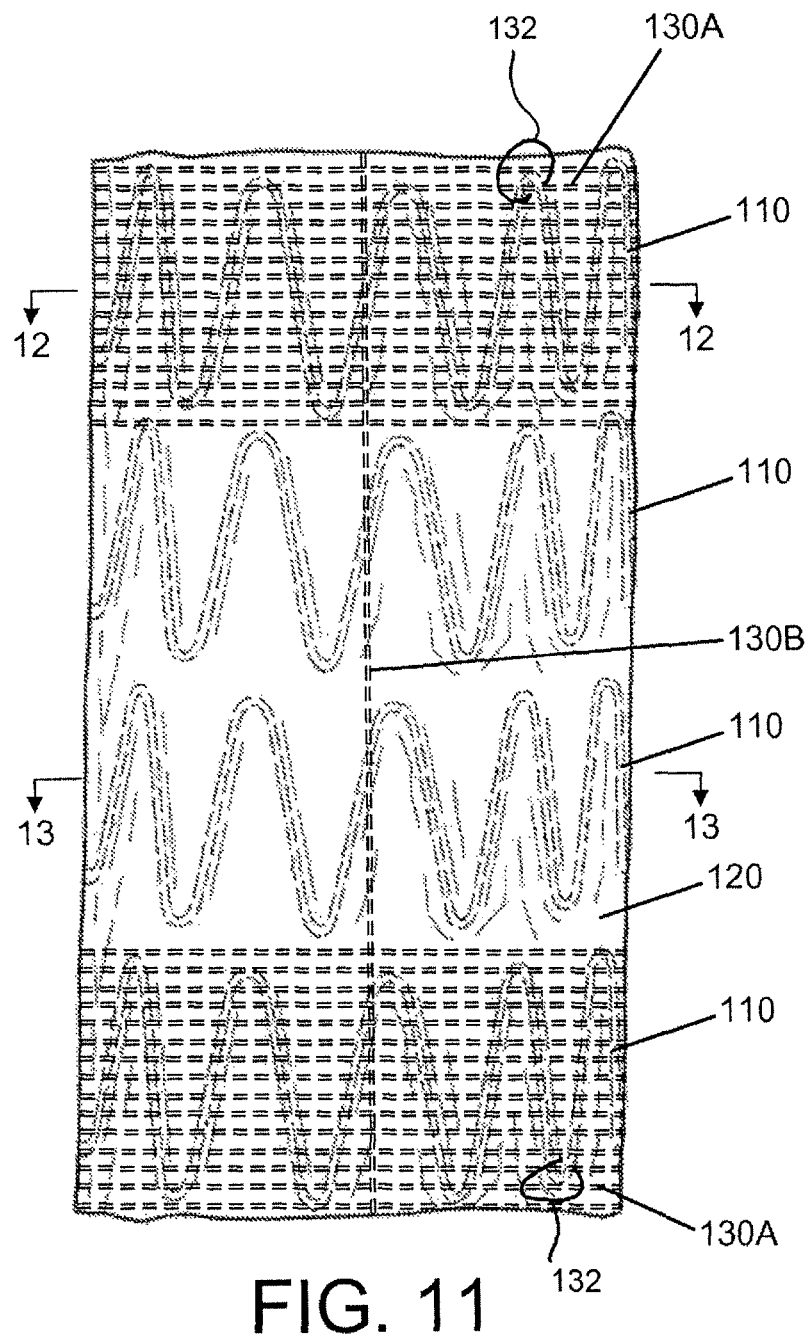
FIG. 11 illustrates one example of an endoluminal prosthesis including a support structure and a fiber matrix encapsulated within a covering.

In another example, the connector segments may be omitted such that the support structure includes a plurality of unconnected ring structures. For example, the support structure may include a plurality of Z-stents spaced from one another along the length of the prosthesis as shown in FIG. 11 and described below. Additionally, or alternatively, one or more of the ring structures may be cut from a tubular cannula. In another example, the support structure may include a plurality of ring structures interconnected by connector segments and one or more unconnected ring structures. For example, a first portion of the support structure may include a plurality of ring structures interconnected by connector segments, and a second portion of the support structure may include one or more ring structures unconnected to the first portion. In one example, the support structure may include an intermediate portion including a plurality of ring structures interconnected by connector segments, a proximal portion including one or more ring structures unconnected to the intermediate portion, and a distal portion including one or more ring structures unconnected to the intermediate portion. The intermediate portion may be positioned longitudinally between the proximal portion and the distal portion.

In one example, the support structure 110 may have a substantially cylindrical shape as shown in FIG. 1. In other words, a transverse cross section of the support structure 110 may have a substantially circular shape. In other examples, the support structure 120 may have any other cross sectional shape including, for example, triangular, rectangular, elliptical, or any other polygonal or non-polygonal shape. A lumen 116 may extend longitudinally within the support structure 110. An inner surface or luminal surface 117 of the support structure 110 may face the lumen 116. In other words, the lumen 116 may be defined by the luminal surface 117 of the support structure 110. The support structure 110 may include an outer surface or abluminal surface 118 positioned opposite the luminal surface 117. In other words, the luminal surface 117 may be positioned inside the support structure, and the abluminal surface 118 may be positioned outside the support structure opposite the luminal surface.

The support structure 110 may add rigidity, expansion force, and/or support to the prosthesis 100. To that end, the support structure 110 may be made from one or more of numerous metals and/or alloys. For example, the support structure 110 may be made from a metallic material such as stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, such as a molybdenum alloy including about 0.4% to about 0.8% of lanthanum oxide ($La_2O_3$), and a nickel-titanium alloy, such as nitinol, or other suitable materials known in the art. In one example, the support structure 110 may include a shape-memory or superelastic material such as nitinol. Use of a shape-memory or superelastic material may enable the support structure 110 to be over-expanded as further described below.

The graft body 120 may be attached to the support structure 110. In one example, the graft body 120 may include an attachment site at which the graft body may be attached to the support structure 110 as further described below. The graft body 120 may be disposed on the luminal surface 117 and/or the abluminal surface 118 of the support structure 110. The graft body 120 may include a tubular body having any suitable shape as described above with reference to the support structure 110. A lumen 122 may extend longitudinally within the graft body 120. The lumen 122 may be at least partially coextensive with the lumen 116 of the support structure 110. The lumen 122 may be configured to permit blood or other body fluids to flow through the prosthesis within the lumen 122.

The graft body 120 may be formed of any suitable graft material. In one example, the graft material may be formed using an electrospinning process as further described below. In other examples, the graft material may be formed using any other suitable method including, for example, dip coating, spray coating, and melt-spinning. Many different types of biocompatible materials may be used to form the graft body 120. The biocompatible material may be substantially non-toxic in the in vivo environment of its intended use, and may be substantially unrejected by the patient's physiological system (i.e., may be non-antigenic). Examples of biocompatible materials from which a graft material may be formed include, for example, polyesters, such as polyethylene terephthalate (PET); fluorinated polymers, such as polytetrafluoroethylene (PTFE) and fibers of expanded PTFE (ePTFE), polyvinylidene fluoride (PVDF); polyurethanes; and polyolefins. Additionally, or alternatively, materials suitable for making graft materials may include polyethylene, polypropylene, polyvinyl chloride (PVC), polyaramids, polyacrylonitrile, nylon, silicone, cellulose, a biological scaffold or bioremodelable material (e.g., small intestine submucosa (SIS), commercially available from Cook Medical Incorporated, Bloomington, Ind.), or biodegradable materials (e.g., polylactides).

Although the discussion in this disclosure will refer to the prosthesis 100, a person having ordinary skill in the art will recognize that the devices and methods described herein may be equally applicable to a prosthesis, such as a stent or stent graft, having any other configuration. For example, the prosthesis may be configured as a bifurcated stent graft, a stent graft having branches, scallops and/or fenestrations, or a prosthesis having any other shape or features. Such devices and methods are contemplated by and within the scope of this disclosure.

Figure 2:
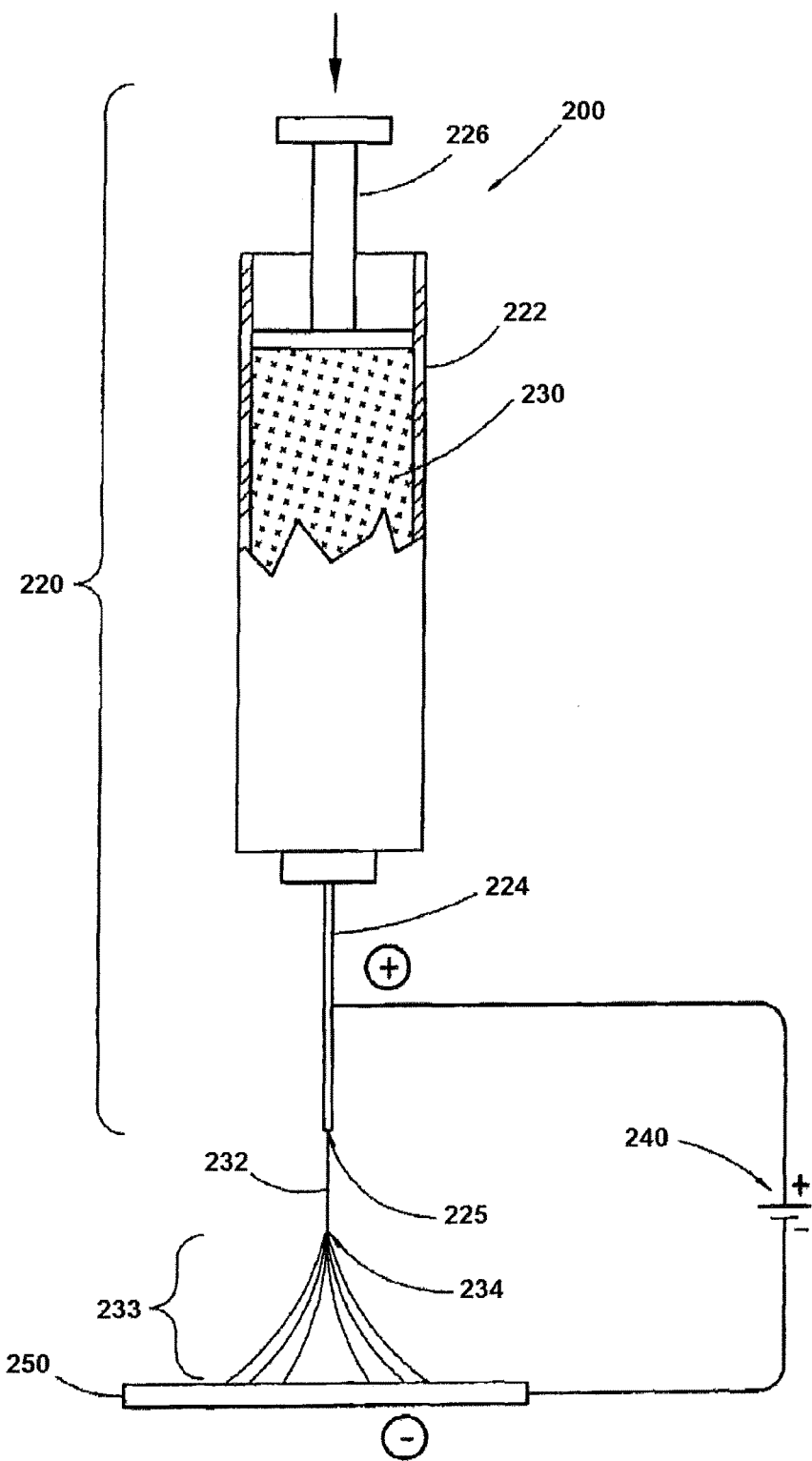
FIG. 2 illustrates one example of an electrospinning apparatus.

FIG. 2 illustrates one example of an electrospinning apparatus 200 for coating an object, such as a substrate or a medical device. The electrospinning apparatus 200 may be similar to that described in U.S. Pat. No. 7,799,261 to Orr et al.; the entire disclosure of this apparatus is incorporated herein in its entirely by reference. For example, the electrospinning apparatus 200 may include a spinneret 220. The spinneret 220 may include a reservoir 222, which may be configured as a syringe-like container as shown in FIG. 2. The reservoir 222 may be fluidly coupled to an orifice 224 to form the spinneret 220. The orifice 224 may be configured as a needle as shown in FIG. 2.

A solution 230 may be loaded into the reservoir 222. Suitable solutions will be discussed in more detail below. The orifice 224 may have a distal opening 225 through which the solution 230 may be driven by a displacement system 226. The displacement system 226 may be configured as any type of controllable, variable rate fluid displacement system. For example, the fluid displacement system 226 may be configured as a plunger as shown in FIG. 2. Preferably, the displacement system 226 may be an automated system to provide a consistent and accurate flow of solution 230 through the orifice 224. In one example, the fluid displacement system 226 may deliver the solution 230 at a delivery rate of about 0 mL/hr to about 25 mL/hr, about 1 mL/hr to about 10 mL/hr, or about 3 mL/hr to about 7 mL/hr.

A voltage source 240 may apply an electric potential across the spinneret 220 and a target 250. In one example, the electric potential may be between about 10 kV and about 35 kV, between about 15 kV and about 30 kV, or between about 20 kV and about 25 kV. The electric potential 240 may aid the displacement system 226 in ejecting the solution 230 from the distal opening 225 of the orifice 224.

The solution may form a charged jet or stream 232 from the distal opening 225 to the target 250. The solution stream 232 may form a conical shape 233, called a Taylor cone, between the spinneret 220 and the target 250. As the solution stream 232 travels away from the opening 225, the cone 233 may begin to splay or stretch at a position 234 between the spinneret 220 and the target 250. In one example, the distance between the distal opening 225 and the target 250 may be between about 0.1 inches to about 6 inches, between about 0.5 inches to about 4 inches, or between about 1 inch to about 2 inches. Position 234 need not be substantially intermediate the distal opening 225 and the target 250, and may be located at any desired distance between the distal opening and the target. The splaying or stretching action may create a plurality of fibers that may or may not dry upon reaching the target 250, depending on the volatility of the chosen solvent. The fibers may contact the target 250 to form a coating of nonwoven fibers thereon. The coating of nonwoven fibers may be configured as a network of fibers deposited on the target 250 to collectively form a sheet of nonwoven fibers.

In one example, an electrospinning apparatus similar to the electrospinning apparatus 200 may be used to prepare an endoluminal prosthesis such as the prosthesis 100 described above. For example, an electrospinning apparatus may be used to form a graft material which may form the graft body 120 as further described below. The graft body 120 may be attached to the support structure 110 to form the prosthesis 100.

Figure 3:
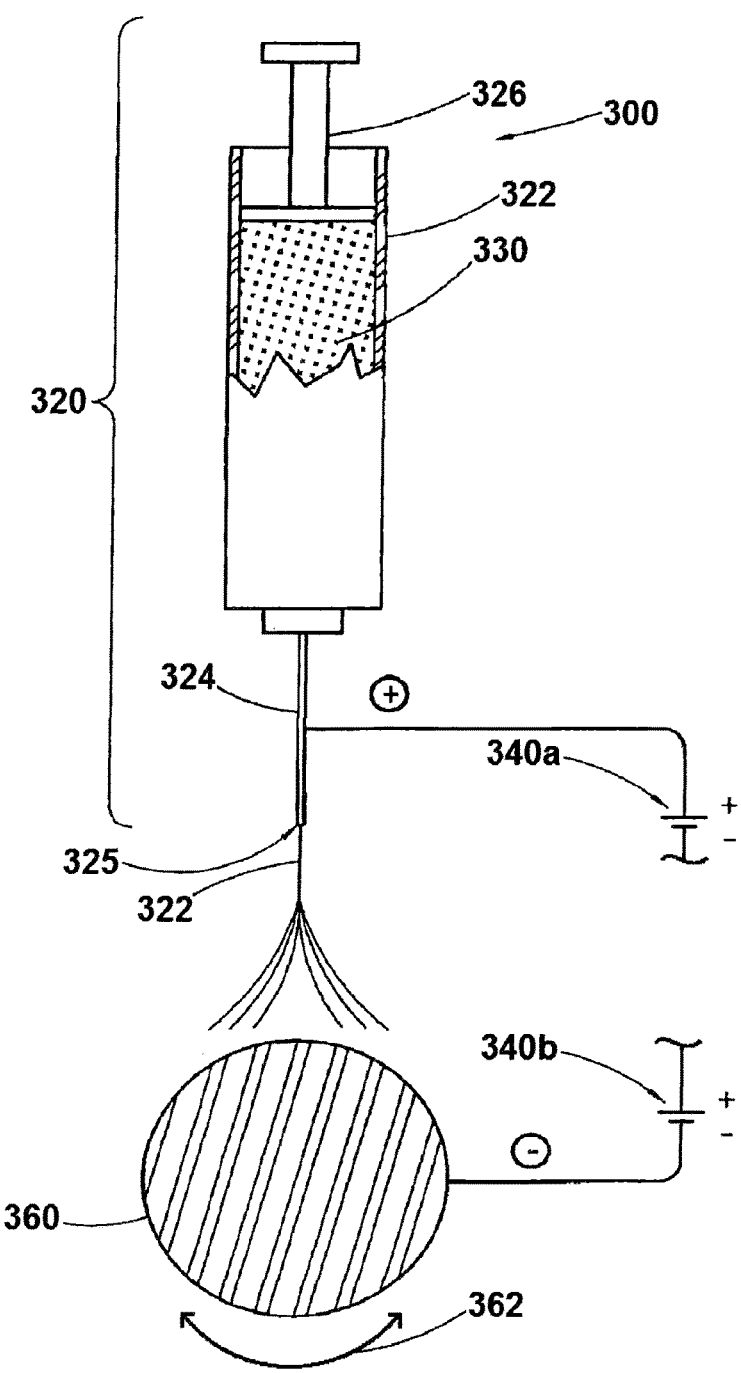
FIG. 3 illustrates an exemplary method step for electrospinning a solution onto an outer surface of a mandrel.

FIG. 3 illustrates one example of an electrospinning apparatus 300, which may be used to prepare the endoluminal prosthesis 100, or a portion thereof, as further described below. For example, the electrospinning apparatus 300 may be used to electrospin a graft material (e.g., PET solution) onto a rotating mandrel to form a covering including a selected graft material. The electrospinning apparatus 300 may be similar to the electrospinning apparatus 200 described above. For example, the electrospinning apparatus 300 may include a spinneret 320 including a reservoir 322 that is fluidly coupled to an orifice 324. A solution 330 may be loaded into the reservoir 322 and driven by a displacement system 326 through a distal opening 325 of the orifice 324. An electric potential may be applied across the spinneret 320 and a mandrel 360. The solution may form a charged jet or stream 332 from the distal opening 325 to the mandrel 360. As the solution stream 332 travels away from the opening 325, the stream may begin to splay or stretch to create a plurality of fibers. The fibers may contact the mandrel 360 to form a coating of nonwoven fibers thereon.

In one example, a voltage source may apply an electric potential across the spinneret 320 and the mandrel 360 as described above with reference to the voltage source 240. In another example, multiple voltage sources may be used to apply the electric potential. For example, a first voltage source 340a may be electrically coupled to the spinneret 320, and a second voltage source 340b may be electrically coupled to the mandrel 360 as shown in FIG. 3. The first voltage source 340a may generate an electric charge on the orifice 324. In other words, the first voltage source 340a may apply an electric potential between the orifice 324 and ground. Similarly, the second voltage source 340b may generate an electric charge on the mandrel 360. In other words, the second voltage source 340b may apply an electric potential between the mandrel 360 and ground.

The electric charge on the mandrel 360 may have an opposite sign relative to the electric charge on the orifice 324. In one example, the orifice 324 may be positively charged (i.e., the sign of the electric charge may be positive), and the mandrel 360 may be negatively charged (i.e., the sign of the electric charge may be negative). In another example, the orifice 324 may be negatively charged, and the mandrel 360 may be positively charged. The magnitude of the electric charge on the orifice 324 may be the same as or different than the magnitude of the electric charge on the mandrel 360. In one example, the magnitude of the electric charge on the orifice 324 relative to ground may be between about 5 kV and about 20 kV, preferably between about 6 kV and about 7.5 kV. Additionally, or alternatively, the magnitude of the electric charge on the mandrel 360 relative to ground may be between about 5 kV and about 20 kV, preferably between about 6 kV and about 7.5 kV. The orifice 324 and the mandrel 360 may have opposing charges such that the electric potential between the orifice and the mandrel may be between about 10 kV and about 40 kV, preferably between about 12 kV and about 15 kV.

In one example, the spinneret 320 may be configured as a 3 mL plastic syringe (e.g., a NORM-JECT® syringe commercially available from Air-Tite Products Co., Virginia Beach, Va.) equipped with a 23-Gauge disposable polymer-hub stainless steel needle. Additionally, or alternatively, the distance between the orifice 324 and the mandrel 360 may be between about 5 cm and about 25 cm, preferably between about 12 cm and about 15 cm. Additionally, or alternatively, the solution 330 may be extruded using a syringe pump at a substantially constant flow rate between about 0.5 mL/h and about 4 mL/h, preferably between about 0.5 mL/h and about 1.5 mL/h. Additionally, or alternatively, each of the first voltage source 340a and the second voltage source 340b may be configured as a high-voltage power supply capable of applying DC voltage up to about 20 kV.

FIG. 3 illustrates the mandrel 360 in a cross-sectional view taken along a plane transverse to the longitudinal axis of the mandrel. In one example, the mandrel 360 may have a substantially cylindrical shape as shown in FIG. 3. In other examples, the mandrel may have any other suitable shape. Preferably, the mandrel 360 may be sized and shaped to correspond to a lumen of a medical device (e.g., the lumen 122 of the graft body 120) as further described below. The mandrel 360 may include an outer surface extending circumferentially and longitudinally along the mandrel.

The mandrel 360 and the spinneret 320 may be movable relative to one another. Such movement may enable the coating of any portion of the outer surface of the mandrel 360. For example, the outer surface may be coated almost entirely, partially, or at discrete locations thereon. For example, the mandrel 360 may be rotatable about the longitudinal axis of the mandrel. In other words, the mandrel 360 may be configured to rotate in a direction indicated by the arrow 362. In one example, the mandrel may be configured to rotate at a speed of between about 80 rpm and about 4000 rpm, or between about 100 rpm and about 500 rpm. The rotational speed of the mandrel 360 may be adjusted to adjust the diameter of the fibers produced during electrospinning. Increasing the rotational speed of the mandrel 360 may reduce the diameter of the fibers. Decreasing the rotational speed of the mandrel 360 may increase the diameter of the fibers. Additionally, or alternatively, the mandrel 360 may be movable in a direction substantially parallel to the longitudinal axis of the mandrel. In other words, the mandrel 360 may be configured to translate (e.g., in a forward or backward longitudinal direction) relative to the spinneret 320. Additionally, or alternatively, the mandrel 360 may be movable in a direction transverse to the longitudinal axis of the mandrel. In other words, the mandrel 360 may be configured to translate (e.g., in an up, down, or sideways transverse direction) relative to the spinneret 320. Such rotation and/or translation (e.g., longitudinal or transverse translation) of the mandrel 360 relative to the spinneret 320 may enable coating of the outer surface of the mandrel, or a portion thereof, with electrospun fibers as further described below. Such a coating may be achieved by any relative motion between the mandrel 360 and the spinneret 320. For example, movement of the mandrel 360 relative to the spinneret 320 may be achieved by maintaining the spinneret in a constant position while moving the mandrel, by maintaining the mandrel in a constant position while moving the spinneret, and/or by moving the mandrel and the spinneret relative to one another. In one example, the mandrel may rotate and the spinneret may translate in a longitudinal direction relative to the mandrel.

The relative movement of the mandrel 360 with respect to the spinneret 320 may influence several properties of the resulting coating of fibers. For example, increasing the speed of the relative motion may cause a reduction in the thickness of the coating. This may be caused, for example, because a portion of the mandrel 360 may be disposed in the path of the stream 332 for a shorter period of time at increased speeds. Additionally, or alternatively, increasing the speed of the relative motion may cause the fibers to be increasingly aligned with one another. This may affect the strength, resiliency, and/or porosity of the coating. Also for example, as the distance between the spinneret 320 and the mandrel 360 is increased, the solution stream 332 may be required to travel a greater distance before reaching the mandrel. This may affect the splaying and/or drying characteristics of the solution stream 332, which may affect the properties of the resultant coating.

In any of the examples described herein, the mandrel 360 may be formed from any suitable conductive material known in the art. For example, the mandrel 360 may be formed from a metallic material such as stainless steel (e.g., electropolished stainless steel) or chrome. In another example, the mandrel 360 may be formed from a non-metallic material such as a conductive plastic material. The mandrel 360 may include a release layer disposed on the outer surface thereof to aid in removing the prosthesis 100, or a portion thereof, from the mandrel as further described below. The release layer may be formed from any material known in the art. Preferably, the release layer may be formed from a non-stick material such as, for example, PTFE, sodium bicarbonate, a silicone lubricant, or any other biocompatible lubricant.

To prepare the prosthesis 100, an inner layer of nonwoven fibers may be formed on the outer surface of the mandrel 360 by electrospinning the solution 330 from the orifice 324 onto the outer surface of the mandrel. In one example, the mandrel 360 may be moved rotationally about the longitudinal axis thereof. The solution 330 may be discharged from the orifice 324 and attracted to the mandrel 360 by the electrical potential applied between the orifice and the mandrel as described above. The rotation of the mandrel 360 may cause the resultant coating of nonwoven fibers to be distributed about the circumference of the mandrel. Additionally, or alternatively, the spinneret 320 may be translated longitudinally relative to the mandrel 360 while discharging the solution 330 from the orifice 324. The translation of the spinneret 320 may cause the resultant coating of nonwoven fibers to be distributed about the length of the mandrel. In one example, the mandrel 360 may be rotated and the spinneret 320 may be translated to form a layer of nonwoven fibers covering substantially the entire circumference of the mandrel along at least a portion of the length of the mandrel.

Figure 4:
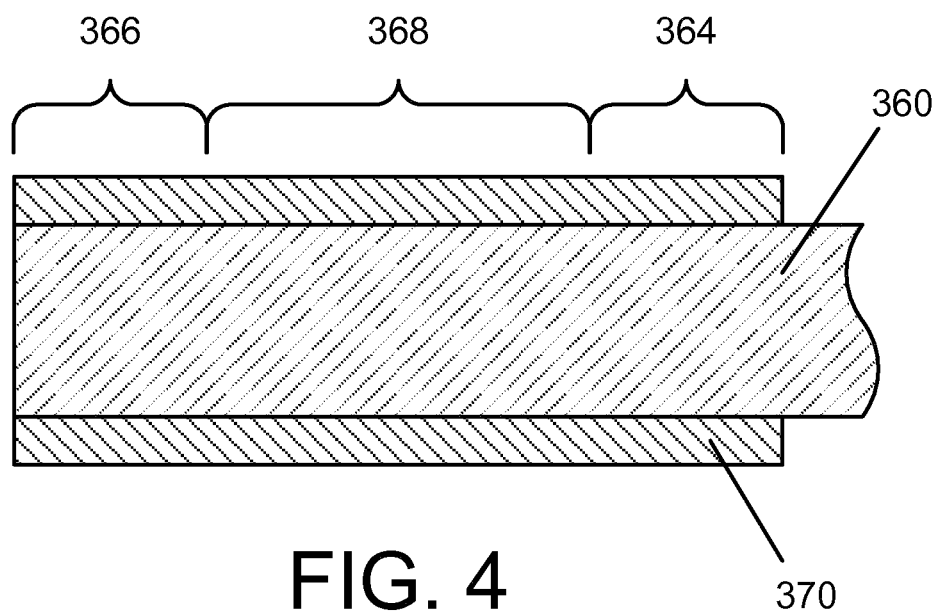
FIG. 4 illustrates one example of a layer of nonwoven electrospun fibers disposed on the outer surface of the mandrel using the method shown in FIG. 3.

FIG. 4 shows a longitudinal cross sectional view of an end portion of the mandrel 360 with an inner layer 370 of nonwoven electrospun fibers disposed on the outer surface thereof. A working length of the mandrel 360 may include a proximal end segment 364, a distal end segment 366, and an intermediate segment 368 positioned between the proximal end segment and the distal end segment. The mandrel 360 may be rotated and the spinneret 320 may be translated while the solution 330 is electrospun onto the outer surface of the mandrel as described above to distribute the electrospun fibers circumferentially and longitudinally about the outer surface of the mandrel. In one example, the solution 330 may be electrospun onto each of the proximal end segment 364, the distal end segment 366, and the intermediate segment 368 of the mandrel 360 such that the inner layer 370 may be disposed upon substantially the entire working length of the outer surface of the mandrel as shown in FIG. 4. In other words, each of the proximal end segment 364, the distal end segment 366, and the intermediate segment 368 of the mandrel 360 may be coated with the electrospun fibers. In one example, the spinneret 320 may be programmed to move longitudinally along the length of the mandrel to focus the fibers produced along substantially the entire mandrel length. The spinneret 320 may make any appropriate number of passes along the length of the mandrel 360 to achieve a coating having a desired thickness. In one example, the coating may have a thickness of between about 10 μm and about 70 μm, typically between about 15 μm and about 25 μm, preferably about 20 μm. During each pass, the spinneret 320 may move longitudinally along substantially the entire working length of the mandrel 360. The number of passes may be increased to increase the thickness of the coating of electrospun fibers or decreased to decrease the thickness of the coating of electrospun fibers.

Figure 5:
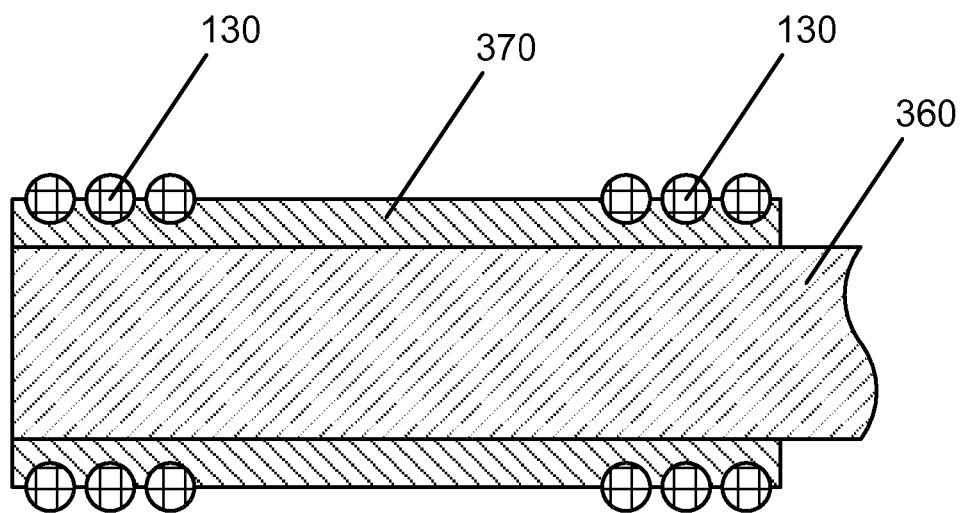
FIG. 5 illustrates one example of a fiber matrix disposed on the layer of nonwoven electrospun fibers of FIG. 4.

A fiber matrix 130 may be placed on the mandrel 360 over the inner layer 370 of nonwoven electrospun fibers as shown in FIG. 5. The fiber matrix 130 may extend longitudinally along substantially all or a portion of the length of the inner layer 370. In some examples, the fiber matrix 130 may include one or more fiber matrix segments as further described below. For example, the fiber matrix 130 may extend longitudinally along a portion of the inner layer 370 near each of the two opposing ends of the inner layer as shown in FIG. 5. In other words, the fiber matrix 130 may include two fiber matrix segments positioned at opposing ends of the inner layer. In other examples, the fiber matrix may extend along any one or more longitudinal and/or circumferential portions of the inner layer 370.

The fiber matrix 130 may be configured as a wrap, mesh, weave, or other arrangement of filamentary or fibrous material. The fiber matrix 130 may be formed from a filamentary or fibrous material, which may be arranged in any suitable pattern as further described below to form the fiber matrix. The filamentary material may be placed on or wound around the inner layer 370 circumferentially and/or longitudinally to form the fiber matrix 130. For example, the filamentary material may be wound around the inner layer 370 (e.g., in a spiral or helical pattern) to form a series of adjacent turns as shown in FIG. 5. Additionally, or alternatively, the filamentary material may be placed in a longitudinal orientation on the inner layer as shown in FIG. 11 and further described below. The filamentary material of the fiber matrix 130 may include an ultra-high molecular weight polyethylene (UHMWPE), PET, a blend of UHMWPE and PET, or any other suitable material. In one example, the filamentary material may include a polymer fiber such as a 10 denier DYNEEMA® thread, commercially available from DSM Dyneema, Stanley, N.C. The fiber matrix 130 may strengthen the prosthesis 100 by reinforcing the graft body 120, or portions thereof, as further described below.

In one example, the fiber matrix 130 may be embedded in the inner layer 370 such that the inner layer extends into one or more spaces or interstices of the fiber matrix. In other words, at least a portion of the inner layer 370 may be positioned within one or more spaces (e.g., formed between adjacent turns) of the fiber matrix 130. This may aid in encapsulating the fiber matrix 130 within the graft body 120 as further described below.

An outer layer of nonwoven electrospun fibers may be formed on the inner layer 370 and/or the fiber matrix 130 by electrospinning the solution 330 from the orifice 324 onto the inner layer and/or the fiber matrix. The inner layer 370 and/or the fiber matrix 130 may be positioned between the spinneret 320 and the mandrel 360, and the solution 330 may be discharged from the spinneret toward the mandrel as described above. The stream 322 may contact the inner layer 370 and/or the fiber matrix 130 to form the outer layer of nonwoven electrospun fibers.

In one example, the mandrel 360 may be moved rotationally about the longitudinal axis thereof, which may cause corresponding rotation of the inner layer 370 and/or the fiber matrix 130. The solution 330 may be discharged from the orifice 324 and attracted to the mandrel 360 by the electrical potential applied between the orifice and the mandrel as described above. The rotation of the inner layer 370 and/or the fiber matrix 130 may cause the resultant coating of nonwoven electrospun fibers to be distributed about the circumference of the inner layer 370 and/or the fiber matrix 130. Additionally, or alternatively, the spinneret 320 may be translated longitudinally relative to the inner layer 370 and/or the fiber matrix 130 while discharging the solution 330 from the orifice 324. The translation of the spinneret 320 may cause the resultant coating of nonwoven fibers to be distributed about the length of the inner layer 370 and/or the fiber matrix 130. In one example, the mandrel 360 may be rotated and the spinneret 320 may be translated to form a layer of nonwoven fibers covering substantially the entire circumference of the inner layer 370 and/or the fiber matrix 130 along at least a portion of the length thereof.

Figure 6:
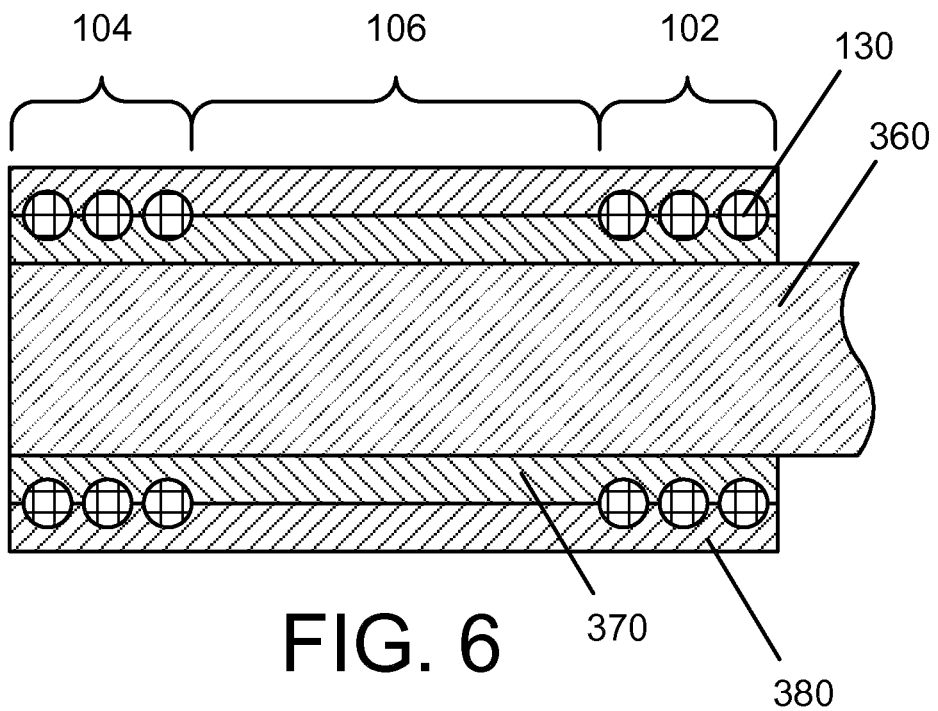
FIG. 6 illustrates one example of a graft body including the fiber matrix of FIG. 5 disposed between two layers of nonwoven electrospun fibers.

FIG. 6 shows a longitudinal cross sectional view of the fiber matrix 130 positioned on the mandrel 360 between the inner layer 370 of nonwoven electrospun fibers disposed on the outer surface of the mandrel and an outer layer 380 of nonwoven electrospun fibers disposed on the inner layer and the fiber matrix. The inner layer 370, the fiber matrix 130, and the outer layer 380 may collectively form the graft body 120. The graft body 120 may include a proximal end segment 102, a distal end segment 104, and an intermediate segment 106 positioned between the proximal end segment and the distal end segment. The proximal end segment 102 of the graft body 120 may be positioned adjacent to the proximal end segment 364 of the mandrel 360; the distal end segment 104 of the graft body may be positioned adjacent to the distal end segment 366 of the mandrel; and/or the intermediate segment 106 of the graft body may be positioned adjacent to the intermediate segment 368 of the mandrel. In other words, each segment of the graft body 120 may be at least partially aligned with the corresponding segment of the mandrel 360 as shown in FIG. 6.

Each of the inner layer 370 and the outer layer 380 may extend longitudinally along each of the proximal end segment 102, the distal end segment 104, and the intermediate segment 106 of the graft body 120 as shown in FIG. 6. In other words, each of the inner layer 370 and the outer layer 380 may extend longitudinally along substantially the entire length of the graft body 120. Additionally, or alternatively, the fiber matrix 130 may extend longitudinally along each of the proximal end segment 102 and the distal end segment 104 of the graft body 120 also as shown in FIG. 6. The intermediate segment 106 of the graft body 120 may be substantially free of the fiber matrix 130. In other words, the graft body 120 may include a fiber matrix segment positioned at the proximal end segment 102 and a fiber matrix segment positioned at the distal end segment 104. The fiber matrix segments may be separated from one another by a longitudinal distance. In other examples, portions of the inner layer 370 and/or the outer layer 380 may be omitted during electrospinning or removed subsequent to electrospinning so that the respective layer extends along a portion of the length of the graft body 120 as further described below. Additionally, or alternatively, the fiber matrix 130 may extend along any portion of the length of the graft body 120 also as further described below.

The fiber matrix 130 may be at least partially encapsulated within a covering formed by the inner layer 370 of nonwoven electrospun fibers and the outer layer 380 of nonwoven electrospun fibers as shown in FIG. 6. In other words, the fiber matrix 130 may be laminated between inner and outer layers of graft material. The inner layer 370 and the outer layer 380 may be joined to one another to form the covering around the fiber matrix 130. For example, the inner layer 370 and the outer layer 380 may contact one another (e.g., through the spaces in the fiber matrix 130 and/or along portions of the graft body 120 that are free of the fiber matrix). The portions of the inner layer 370 and the outer layer 380 in contact with one another may bond to one another to join the inner layer and the outer layer to one another. The inner layer 370 and the outer layer 380 may be joined to one another during the electrospinning process without an additional bonding process (e.g., heat or pressure bonding) and/or without additional bonding materials (e.g., adhesives, sutures, staples, or clips). The fiber matrix 130 may extend circumferentially and longitudinally within the covering formed by the inner layer 370 and the outer layer 380 as shown in FIG. 6. In other words, the fiber matrix 130 may extend angularly (e.g., relative to a reference direction transverse to the longitudinal axis of the graft body) and longitudinally within the covering formed by the inner layer 370 and the outer layer 380.

The graft body 120 (e.g., the inner layer 370, the fiber matrix 130, and the outer layer 380) may be removed from the mandrel 360. To that end, the mandrel 360 may include a release layer applied to the outer surface thereof. The release layer may reduce the attractive force (e.g., adhesive force) or the frictional force between the graft body 120 and the outer surface of the mandrel 360 to aid in removing the prosthesis 100 from the mandrel in an undamaged condition.

Figure 7:
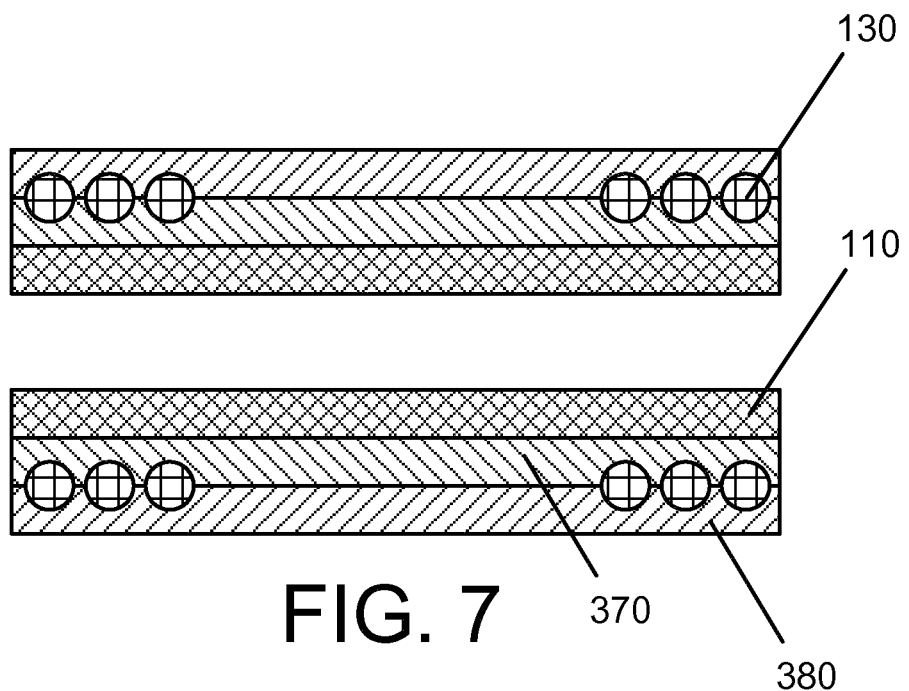
FIG. 7 illustrates one example of a support structure attached to the graft body of FIG. 6.

The graft body 120 may be attached to the support structure 110 to form the prosthesis 100 as shown in FIG. 7. The support structure 110 may be positioned within the lumen 122 of the graft body 120 (e.g., on an inner surface of the graft body) or external to the graft body (e.g., on an outer surface of the graft body). Additionally, or alternatively, portions of the support structure may be positioned within the lumen of the graft body, and portions of the support structure may be positioned external to the graft body. For example, the support structure may include a plurality of support structures (e.g., a plurality of stents), one or more of the support structures may be positioned within the lumen of the graft body, and one or more of the support structures may be positioned external to the graft body. Additionally, or alternatively, the support structure, or a portion thereof, may be encapsulated within the graft body as further described below. The graft body 120 may be attached to the support structure 110 in any suitable manner including, for example, bonding (e.g., with an adhesive or a bonding tape), suturing, stapling, clipping, or any other attachment method. In one example, the graft body 120 may be attached to the support structure 110 by suturing at the fiber matrix 130 as further described below.

Figure 8:
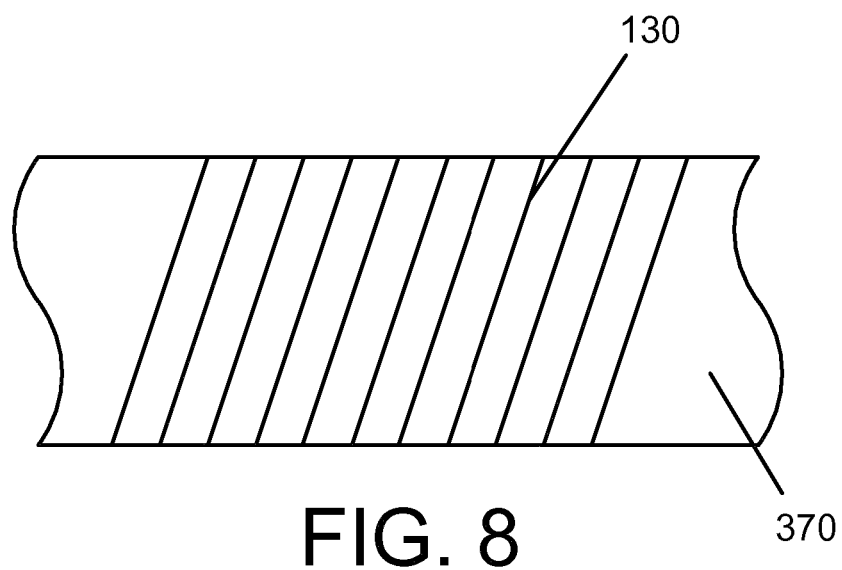
FIG. 8 illustrates one example of a fiber matrix disposed on a layer of nonwoven electrospun fibers.

The filamentary material may be arranged in any suitable configuration to form the fiber matrix 130. In one example, the filamentary material may be wound around the mandrel 360 and/or the inner layer 370 of nonwoven electrospun fibers in a spiral or helical pattern to form the fiber matrix 130 as shown in FIG. 8. The spiral or helical pattern may have any suitable spacing between adjacent windings or turns. In other words, the spiral or helical pattern may have any suitable pitch. In one example, the adjacent windings may be in abutting contact with one another such that the fiber matrix 130 forms a substantially continuous surface along the length thereof. In other examples the adjacent windings may be spaced from one another such that the fiber matrix 130 forms a discontinuous surface along the length thereof. The discontinuous surface may include one or more spaces between adjacent windings. The inner layer 370 and/or the outer layer 380 of nonwoven electrospun fibers may extend into the spaces between adjacent windings as described above.

Figure 9:
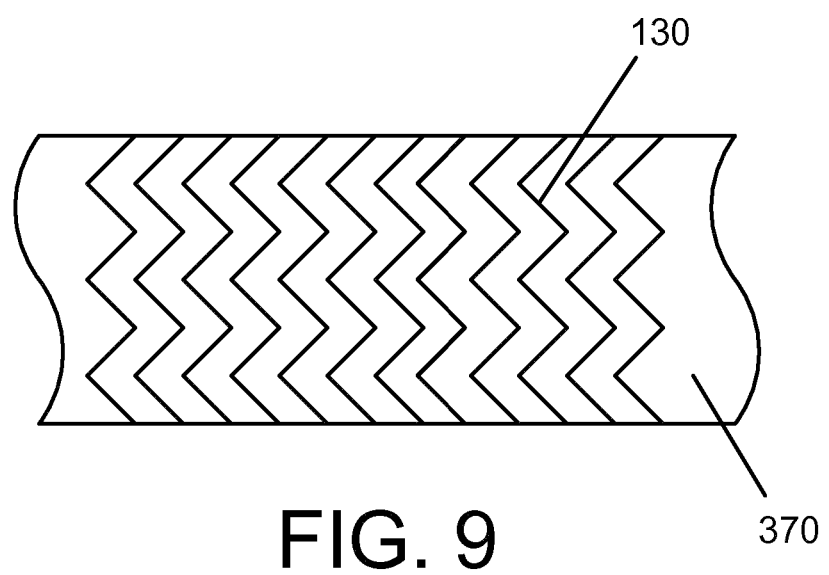
FIG. 9 illustrates another example of a fiber matrix disposed on a layer of nonwoven electrospun fibers.

In another example, the filamentary material may be disposed on the mandrel 360 and/or the inner layer 370 of nonwoven electrospun fibers in a zig-zag pattern to form the fiber matrix 130 as shown in FIG. 9. The zig-zag pattern may include a plurality of substantially straight segments interconnected by a plurality of bends. Additionally, or alternatively, the zig-zag pattern may at least partially encircle the mandrel 360 and/or the inner layer 370 in a circumferential or angular direction. The zig-zag pattern may be formed from a single filamentary member wrapped around the mandrel 360 and/or the inner layer 370 in successive turns or by a plurality of filamentary members each forming one or more rings extending partially or entirely around the mandrel and/or the inner layer. A fiber matrix having such a zig-zag configuration may be capable of stretching circumferentially during expansion of the support structure 110 within the graft body 120. In other words, the fiber matrix

130 may be stretchable in a circumferential direction (e.g., by flexing of the bends) to accommodate radial expansion of the prosthesis 100 during deployment thereof.

Figure 12:
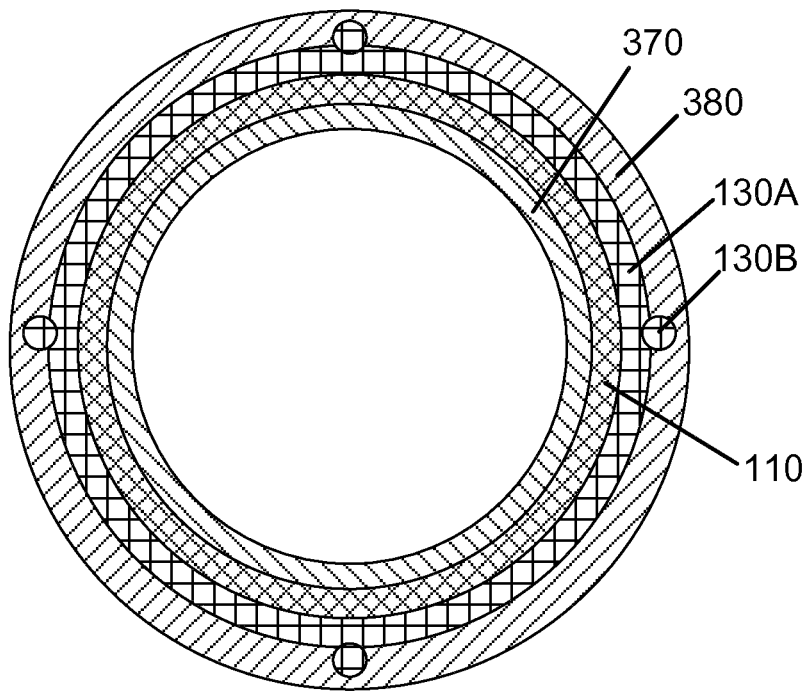
FIG. 12 illustrates a transverse cross sectional view taken along line 12-12 of FIG. 11.
Figure 13:
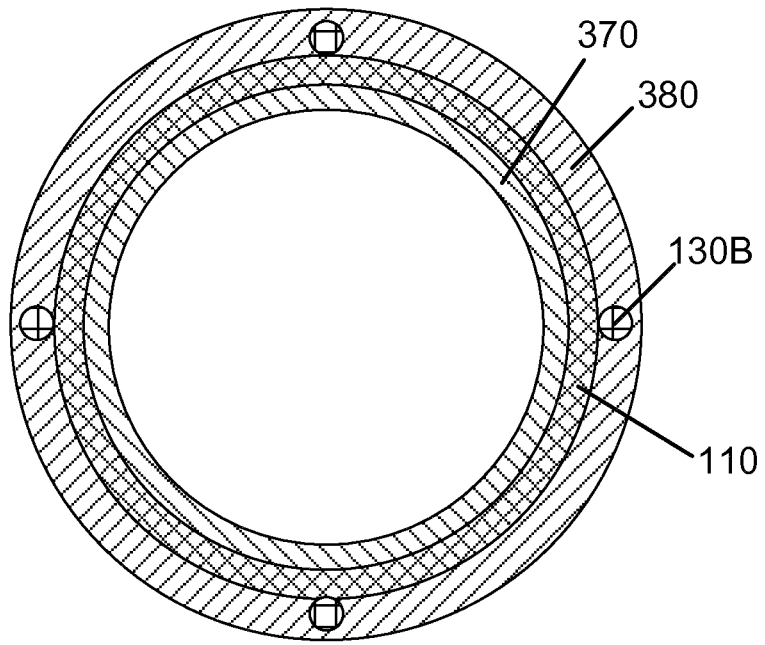
FIG. 13 illustrates a transverse cross sectional view taken along line 13-13 of FIG. 11.

In another example, the filamentary material may be disposed on the mandrel 360 and/or the inner layer 370 of nonwoven electrospun fibers in a longitudinal orientation as further described below. In other examples, the filamentary material may be disposed on the mandrel and/or the inner layer of graft material in any other suitable pattern such as, for example, a wave-like pattern (e.g., resembling a sine wave or a sinusoid). In other examples, the fiber matrix may include multiple fiber matrix segments in different patterns or orientations. For example, the fiber matrix may include a fiber matrix segment extending circumferentially along the graft body (e.g., as shown in any of FIGS. 5-12 and 14-15) and a fiber matrix segment extending longitudinally along the graft body (e.g., as shown in FIGS. 11-13) as further described below.

In one example, the fiber matrix 130 may extend along substantially the entire length and/or circumference of the graft body 120. In other examples, the fiber matrix 130 may extend along a portion of the length and/or circumference of the graft body 120. In other words, the fiber matrix 130 may be disposed at one or more discrete longitudinal positions along the length of the graft body 120 and/or at one or more discrete circumferential positions around the circumference of the graft body. At least a portion of the graft body 120 may be free of the fiber matrix 130. The fiber matrix 130 may include one or more segments that are longitudinally shorter than the graft body 120 (e.g., one or more transverse fiber matrix segments as further described below). Additionally, or alternatively, the fiber matrix 130 may include one or more segments that are circumferentially shorter than the graft body 120 (e.g., one or more longitudinal fiber matrix segments as further described below).

In one example, the fiber matrix 130 may include a plurality of segments spaced from one another along the length of the graft body 120. For example, the fiber matrix 130 may be positioned at one or more of the proximal end portion 102, the distal end portion 104, or the intermediate portion 106 of the graft body 120. In one example, the fiber matrix 130 may be positioned adjacent to an end portion of the graft body 120. For example, the proximal end portion 102 If the graft body 120 may include a segment of the fiber matrix 130. Additionally, or alternatively, each of the distal end portion 104 and the intermediate portion 106 may be substantially free of the fiber matrix, or one or more of the distal end portion and the intermediate portion may include another segment of the fiber matrix. The fiber matrix 130, or segment thereof, disposed at the proximal end portion 102 may help to stiffen the region of the graft body 120 at the end of the prosthesis 100 (e.g., a proximal lip of the graft). This may aid in preventing the graft material at the end of the prosthesis 100 from in-folding, which may result in a type I endoleak. Additionally, or alternatively, the fiber matrix 130 may be disposed at any other longitudinal and/or circumferential position to reinforce or strengthen any portion of the prosthesis 100. In other examples, the graft body may include any number of fiber matrix segments spaced from one another by any longitudinal and/or circumferential distance.

In one example, the fiber matrix 130 may be configured to strengthen the graft body 120 at one or more attachment sites. The attachment sites may be positions along the graft body 120 where the graft body may be attached to a support structure to form a covered stent. In one example, the attachment sites may be configured as suture zones, which may be positions along the graft body 120 where the graft body may be sutured to a support structure. The graft body 120 may be sutured to a support structure using any suitable suturing technique, and the sutures may be positioned at the reinforced suture zones. Reinforcing the suture zones with the fiber matrix 130 may aid in preventing tearing of the graft material near the sutures. In one example, the fiber matrix 130 may have a color that is different than the color of the graft material. The colored fiber matrix may enable easy identification of the suture zones during the manufacturing process to aid in attaching the graft body 120 to a support structure. In other words, the colored fiber matrix may aid in identifying the suture zones (e.g. by distinguishing the suture zones from the remainder of the graft body) to aid in attaching the graft body 120 to a support structure during manufacture of a covered stent.

Figure 10:
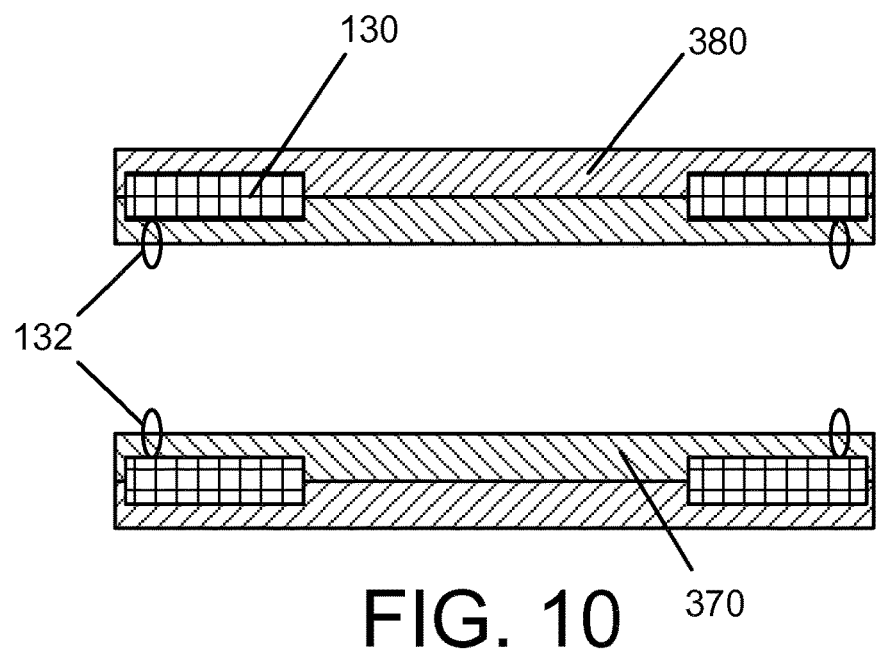
FIG. 10 illustrates one example of a graft body including a fiber matrix with a plurality of loop points.

In one example, the fiber matrix 130 may include one or more loop points 132 as shown in FIG. 10. The loop point 132 may be configured as a portion of the filamentary material of the fiber matrix 130 which may be formed into a loop or ring structure extending away from the surface of the fiber matrix (e.g., in a direction transverse to the longitudinal axis of the graft body). The loop point 132 may extend inward toward the lumen of the graft body as shown in FIG. 10 or outward away from the lumen of the graft body. The inward facing loop point may be preferred in applications in which the graft body will be disposed on the abluminal surface of a support structure. Additionally, or alternatively, the outward facing loop point may be preferred in applications in which the graft body will be disposed on the luminal surface of a support structure. In one example, the loop point 132 may be formed integrally with the fiber matrix (e.g., as the filamentary material is wound around the mandrel and/or the inner layer of nonwoven electrospun fibers). In another example, the loop point 132 may be formed as a discrete loop of filamentary material which may be attached to the fiber matrix 130. The fiber matrix 130 may include any number of loop points 132 positioned at any longitudinal and/or circumferential positions along the fiber matrix. Loop points 132 may be included on a fiber matrix having any configuration described herein (e.g., including one or more transverse fiber matrix segments and/or one or more longitudinal fiber matrix segments).

In one example, a portion of the support structure may be received within one or more of the loop points 132 to attach the graft body to the support structure. For example, the loop points 132 may be positioned at an end portion of the graft body, and one or more apices of the support structure may be received within the loop points to attach the end portion of the graft body to the support structure. In another example, the loop points 132 may be sutured to the support structure to attach the graft body to the support structure. In other words, the loop points 132 may be used to tack stitch the graft body to the support structure. The suture may extend through the loop point and a portion of the support structure to attach graft body to the support structure. In this manner, the suture may not penetrate the graft material of the graft body. In other words, suturing the loop points 132 to the support structure may enable the graft body to be sutured or stitched to the support structure while remaining substantially free of suture holes formed in the graft material of the graft body. This may enable the graft body to be sutured to the support structure while remaining substantially nonporous.

In one example, the support structure 110 may be at least partially encapsulated within the graft body 120. FIG. 11 shows one example of the support structure 110 at least partially encapsulated between the inner layer 370 and the outer layer 380 of nonwoven electrospun fibers. The support structure 110 and the fiber matrix 130 within the graft body 120 are shown in phantom lines in FIG. 11. FIGS. 12-13 are transverse cross sectional views of the prosthesis 100 taken along lines 12-12 and 13-13, respectively, of FIG. 11. To encapsulate the support structure 110, the support structure may be placed on the mandrel 360 over the layer 370 of electrospun fibers and/or the fiber matrix 130. The outer layer 380 may be electrospun over the support structure so that the support structure is positioned between the inner layer 370 and the outer layer as shown in FIGS. 11-13.

The fiber matrix 130 may include a plurality of fiber matrix segments. For example, the fiber matrix 130 may include a transverse or circumferential fiber matrix segment 130A and a longitudinal fiber matrix segment 130B as shown in FIGS. 11-13. The transverse fiber matrix segment 130A may extend in a transverse (e.g., circumferential or angular) direction along the graft body 120. In one example, the transverse fiber matrix segment 130A may extend in a transverse and longitudinal direction (e.g., in a spiral or helical pattern or a series of longitudinally spaced rings) as shown in FIG. 11 and described above. The transverse fiber matrix segment 130A may include a plurality of turns extending angularly around the longitudinal axis of the graft body 120. In one example, the transverse fiber matrix segment 130A may extend along a portion of the length of the prosthesis 100. In other words, the transverse fiber matrix segment 130A may have a longitudinal length that is less than the length of the prosthesis 100. In one example, the transverse fiber matrix segment 130A may include a plurality of transverse fiber matrix segments spaced from one another along the length of the prosthesis as shown in FIG. 11.

Additionally, or alternatively, the longitudinal fiber matrix segment 130B may extend in a longitudinal direction along the graft body 120. In one example, the longitudinal fiber matrix segment 130B may include a substantially linear filamentary member extending along the length of the prosthesis as shown in FIG. 11. In one example, the longitudinal fiber matrix segment 130B may include a substantially linear segment extending along the length of the prosthesis in a direction substantially parallel to the longitudinal axis of the graft body 120. In one example, the longitudinal fiber matrix segment 130B may extend in a primarily longitudinal direction. In other words, the longitudinal fiber matrix segment may extend primarily longitudinally, even though the longitudinal fiber matrix may extend transversely to some extent. To that end, the longitudinal fiber matrix segment 130B may extend less than about 360 degrees (e.g., less than one turn), less than about 90 degrees, less than about 30 degrees, and/or less than about 15 degrees around the longitudinal axis of the graft body 120.

The longitudinal fiber matrix segment 130B may extend along substantially the entire length of the prosthesis 100. In one example, the longitudinal fiber matrix segment 130B may include a plurality of longitudinal fiber matrix segments spaced from one another circumferentially about the prosthesis. For example, the longitudinal fiber matrix segment may include four longitudinal fiber matrix segments spaced from one another by about 90 degrees as shown in FIGS. 12-13. Each longitudinal fiber matrix segment may be formed from a discrete length of filamentary material. Alternatively, two or more longitudinal fiber matrix segments may be formed from a unitary length of filamentary material. To that end, the longitudinal fiber matrix segment may include a series of substantially linear longitudinal fiber matrix segments joined to one another by one or more bends (e.g., positioned near the proximal and/or distal ends of the prosthesis).

The transverse fiber matrix segment 130A and the longitudinal fiber matrix segment 130B may at least partially overlap one another as shown in FIG. 11. Alternatively, the transverse fiber matrix segment and the longitudinal fiber matrix segment may extend along discrete longitudinal portions of the prosthesis such that they do not overlap one another. The transverse fiber matrix segment and the longitudinal fiber matrix segment may be formed from discrete lengths of filamentary material. Alternatively, the transverse fiber matrix segment and the longitudinal fiber matrix segment may be formed from a unitary length of filamentary material (e.g., with discrete portions of the unitary length of filamentary material arranged in different orientations). The longitudinal fiber matrix segment 130B may aid in maintaining alignment of the support structure during deployment of the prosthesis. For example, the longitudinal fiber matrix segment 130B may aid in preventing twisting or torquing of the graft body 120.

The filamentary material of the fiber matrix segment may be selected to achieve a desired property. For example, the filamentary material may include an elastomeric material (e.g., nylon or rubber) that may enhance the flexibility of the graft body or a portion thereof. Additionally, or alternatively, the filamentary material may include a relatively strong material (e.g., UHMWPE) that may enhance the strength of the graft body or a portion thereof. Additionally, or alternatively, discrete segments of the fiber matrix may be formed from different filamentary materials, or combinations thereof. For example, one transverse and/or longitudinal fiber matrix segment may be formed from a first filamentary material, and another transverse and/or longitudinal fiber matrix segment may be formed from a second filamentary material that is different than the first filamentary material. In this manner, discrete longitudinal and/or circumferential portions of the graft body may have different mechanical properties (e.g., elasticity and/or strength).

In one example, the support structure may include a plurality of support structures spaced from one another along the length of the prosthesis as shown in FIG. 11. The transverse fiber matrix segment 130A may be longitudinally aligned with one or more of the plurality of support structures (e.g., a proximal stent and a distal stent as shown in FIG. 11). In this manner, the transverse fiber matrix segment 130A may serve as an attachment site at which the graft body 120 and the support structure 110 may be attached (e.g., sutured) to one another as described above. Additionally, or alternatively, one or more longitudinal segments of the graft body 120 longitudinally aligned with one or more of the support structures (e.g., one or more intermediate or body stents as shown in FIG. 11) may be free of the transverse fiber matrix segment. In this manner, the thickness of the prosthesis may be reduced and/or the flexibility of the prosthesis may be improved as further described below.

In one example, the support structure 110 may be encapsulated within the graft body 120 so that the graft body and the support structure are attached to one another without the use of any attachment material (e.g., suture, tape, such as PTFE-FEP bonding tape, glue, or lamination material) or additional processing steps (e.g., mechanical attachment, pressure bonding, chemical treatment, or thermal bonding). In other words, the prosthesis may be substantially free of an extrinsic attachment mechanism. This may enable a prosthesis having a reduced profile (e.g., because such attachment material may increase the thickness of the covering) and/or increased flexibility (e.g., because such attachment material may increase the stiffness of the covering). In other examples, the graft body 120 may be attached to the support structure 110 with an attachment material (e.g., one or more sutures) to reinforce or strengthen the attachment between the graft body and the support structure. In one example, the support structure 110 may be encapsulated within the graft body 120 and attached to the graft body with an attachment material.

In one example, the support structure 110 may have a relaxed diameter. The support structure 110 may be configured to expand to the relaxed diameter after compressing the support structure to a compressed diameter (e.g., for introducing the support structure into a body lumen in a conventional manner) and releasing the support structure in the compressed configuration. Additionally, or alternatively, the support structure 110 may be over-expandable to a diameter that is greater than the relaxed diameter (e.g., by exerting a radially outward force on the support structure in the relaxed diameter). The support structure 110 may contract toward the relaxed diameter upon releasing the support structure in the over-expanded configuration. The support structure 110 may be over-expanded for placement over the mandrel 360. In other words, the support structure 110 may be over-expanded to a first diameter that is greater than the relaxed diameter of the support structure and placed over the mandrel 360. The support structure 110 may be allowed to contract to a second diameter that is smaller than the first diameter to contact the inner layer 370 and/or the fiber matrix 130 on the mandrel 360. The second diameter may be greater than the relaxed diameter of the support structure 110. In other words, the support structure 110 may be over-expanded even in the second diameter configuration. Upon removal of the support structure 110 and the graft body 120 from the mandrel 360, the support structure may contract to the relaxed diameter. This may reduce the tension of the graft body 120 on the support structure 110, which may help to prevent damaging the graft body upon expansion and/or flexing of the support structure.

In some examples, the inner layer 370 or the outer layer 380 of the graft body 120 may be omitted. In other words, the graft body 120 may include a single layer of graft material, and the fiber matrix 130 may be disposed on an inner surface or an outer surface of the layer of graft material. In one example, the graft body may include an inner layer 370 of nonwoven electrospun fibers and the fiber matrix 130 disposed on an outer surface thereof. The graft body may be formed generally as described above, except that the outer layer 380 may be omitted. In another example, the graft body may include an outer layer 380 of nonwoven electrospun fibers and the fiber matrix 130 disposed on an inner surface thereof. To form the graft body, the fiber matrix may be formed on the mandrel 360 (e.g., by winding the filamentary material around the mandrel), and the outer layer 380 may be formed on an outer surface of the fiber matrix using any suitable method. Using a single layer of graft material may enable the graft body to have a reduced profile (e.g., a reduced thickness).

Figure 14:
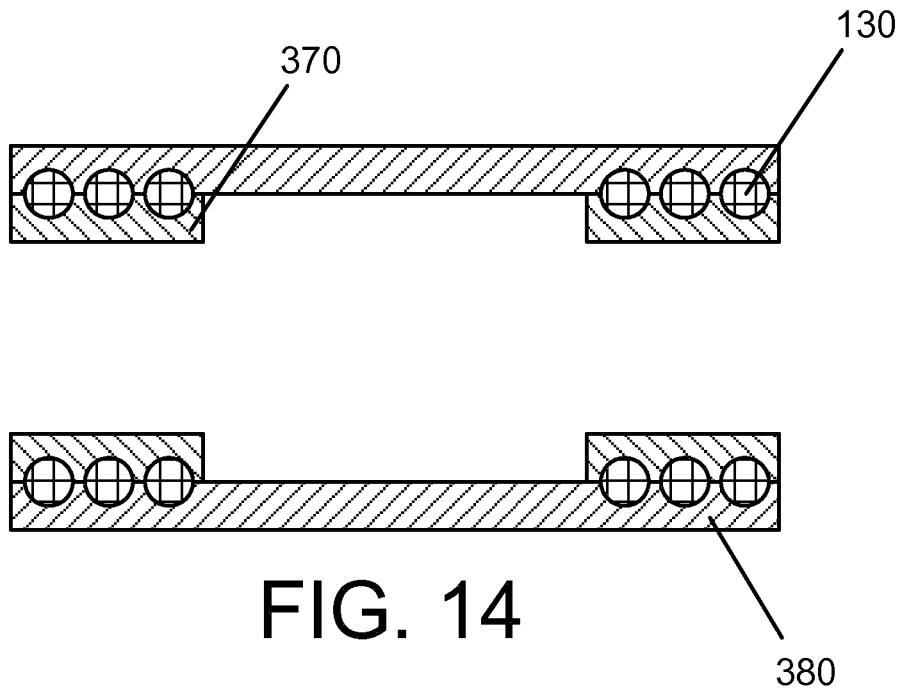
FIG. 14 illustrates one example of a graft body including an inner layer of nonwoven electrospun fibers extending along a portion of the length of the graft body.

In some examples, the inner layer 370 and/or the outer layer 380 of nonwoven electrospun fibers may extend longitudinally along a portion of the length of the graft body. In one example, the inner layer 370 may extend longitudinally along each of the proximal end segment 102 and the distal end segment 104, but not along the intermediate segment 106 of the graft body 120 as shown in FIG. 14. In other words, each of the proximal end segment 102 and the distal end segment 104 of the graft body 120 may include the inner layer 370, and the intermediate segment 106 of the graft body may be free of the inner layer. The proximal end segment 102 and the distal end segment 104 of the prosthesis may include at least a portion of the fiber matrix 130 (e.g., the transverse fiber matrix segment) so that the fiber matrix is encapsulated between the inner and outer layers as described above.

The inner layer 370 of nonwoven electrospun fibers may be formed on a portion of the working length of the mandrel 360 to form an inner layer extending longitudinally along a portion of the length of the graft body. In one example, substantially the entire working length of the mandrel 360 may be coated with the inner layer 370 as described above. A portion of the inner layer 370 may be selectively removed from the mandrel. For example, a central portion of the inner layer 370 disposed on the intermediate segment 368 of the mandrel 360 may be removed. The central portion of the inner layer 370 may be removed from the mandrel 360 in any suitable manner such as, for example, severing the inner layer at the ends of the intermediate segment 368 (e.g., between the intermediate segment and each of the proximal end segment 364 and the distal end segment 366) and lifting the central portion of the inner layer from the mandrel.

In another example, the inner layer 370 may be formed on a portion of the working length of the mandrel 360 by controlling the movement of the spinneret 320 and the mandrel 360 relative to one another during the electrospinning process as described above. For example, the longitudinal translation of the spinneret 320 may be limited such that substantially no fibers are electrospun onto the intermediate segment 368 of the mandrel. Additionally, or alternatively, the flow of the solution 330 from the orifice 325 may be interrupted (e.g., stopped and restarted) during the electrospinning process to avoid electrospinning fibers onto the intermediate segment 368 of the mandrel 360. In other words, a portion of the inner layer 370 may be electrospun on the proximal end segment 364 of the mandrel 360, and another portion of the inner layer may be electrospun on the distal end segment 366. The flow of the solution 330 may be interrupted as the spinneret moves across the intermediate segment 368 of the mandrel 360 so that substantially no fibers are electrospun onto the intermediate segment.

In yet another example, the inner layer 370 may be formed on a portion of the working length of the mandrel 360 by shielding a portion of the mandrel during the electrospinning process. For example, a portion of the mandrel 360 (e.g., the intermediate segment 368) may be covered with a shielding material (e.g., a removable non-adhesive material, such as TEFLON® tubing, or a band of insulating tape) so that the covered portion of the mandrel remains uncoated during the electrospinning process. In still another example, a diffusion template may be used to shield a portion of the mandrel. For example, the diffusion template may be configured as a plate including an opening formed therein. The plate may be placed between the spinneret 320 and the mandrel 360 to obstruct the electrospun fibers from reaching a determined portion (e.g., the intermediate segment 368) of the mandrel.

The fiber matrix 130 may be placed on the mandrel 360 over the inner layer 370 of nonwoven electrospun fibers. The outer layer 380 of nonwoven electrospun fibers may be formed on the inner layer 370 and/or the fiber matrix 130 as described above. In this manner, a longitudinal portion of the graft body may be free of the inner layer 370, and the fiber matrix 130 may be at least partially encapsulated between the inner layer and the outer layer 380.

Figure 15:
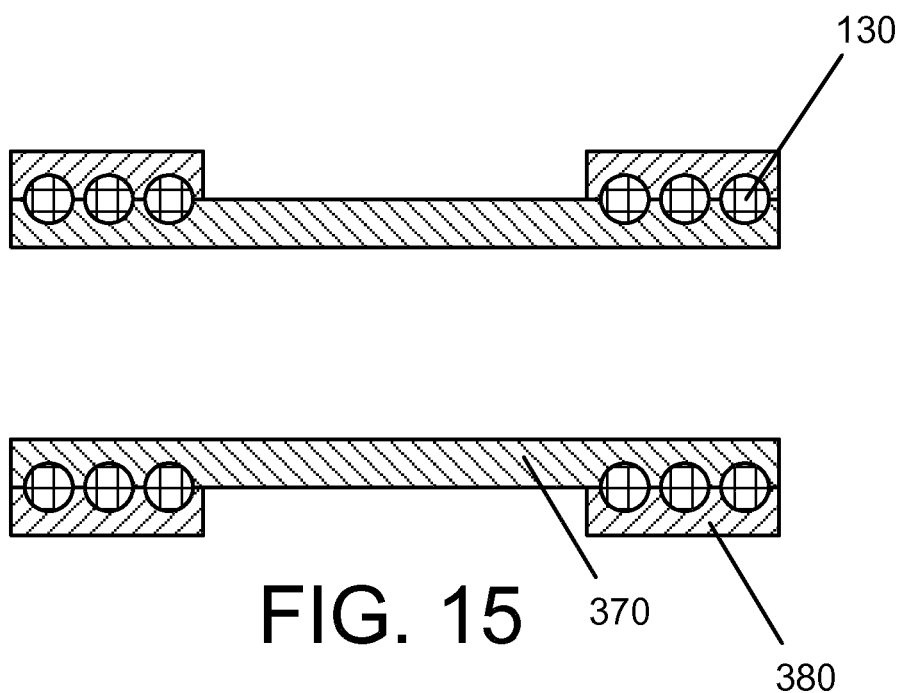
FIG. 15 illustrates another example of a graft body including an outer layer of nonwoven electrospun fibers extending along a portion of the length of the graft body.

In another example, the outer layer 380 may extend longitudinally along each of the proximal end segment 102 and the distal end segment 104, but not along the intermediate segment 106 of the graft body 120 as shown in FIG. 15. In other words, each of the proximal end segment 102 and the distal end segment 104 of the graft body 120 may include the outer layer 380, and the intermediate segment 106 of the graft body may be free of the outer layer. The proximal end segment 102 and the distal end segment 104 of the prosthesis may include at least a portion of the fiber matrix 130 so that the fiber matrix is at least partially encapsulated between the inner and outer layers as described above.

The outer layer 380 of nonwoven electrospun fibers may be formed on a portion of the inner layer 370 and/or the fiber matrix 130 to form an outer layer extending longitudinally along a portion of the length of the graft body. The inner layer 370 may be disposed upon substantially the entire working length of the mandrel 360, and the fiber matrix 130 may be disposed on the inner layer as described above. The outer layer 380 may be disposed upon a portion of the length of the inner layer 370 and/or the fiber matrix 130. In one example, substantially the entire length of the inner layer 370 and/or the fiber matrix 130 may be coated with the outer layer 380 of nonwoven electrospun fibers as described above. A portion of the outer layer 380 may be removed from the inner layer 370 and/or the fiber matrix 130. For example, a central portion of the outer layer 380 disposed longitudinally between adjacent fiber matrix segments may be removed. The central portion of the outer layer 380 may be removed in any suitable manner as described above with reference to removing a portion of the inner layer 370 from the mandrel 360. In another example, the outer layer 380 may be formed on a portion of the length of the inner layer 370 and/or the fiber matrix 130 by controlling the movement of the spinneret 320 and the mandrel 360 relative to one another during the electrospinning process as described above. For example, the longitudinal translation of the spinneret 320 may be limited and/or the flow of solution 330 may be interrupted such that substantially no fibers are electrospun onto the central portion of the inner layer 370. In yet another example, the outer layer 380 may be formed on a portion of the length of the inner layer 370 and/or the fiber matrix 130 by shielding a portion of the inner layer and/or the fiber matrix during the electrospinning process as described above. For example, a portion of the inner layer 370 (e.g., the central portion of the inner layer) may be covered with a length of removable, non-adhesive material (e.g., TEFLON® tubing) which may keep electrospun material off of the portion of the inner layer so that the covered portion of the inner layer remains uncoated during the electrospinning process. In this manner, the fiber matrix 130 may be at least partially encapsulated within the covering formed by the inner layer 370 and the outer layer 380 of nonwoven electrospun fibers.

In other examples, any longitudinal portion of the graft body 120 may include the inner layer 370 without the outer layer 380, the outer layer 380 without the inner layer 370, or both the inner layer 370 and the outer layer 380 of nonwoven electrospun fibers. The portions of the graft body 120 including the fiber matrix 130 or a segment thereof (e.g., a transverse fiber matrix segment and/or a longitudinal fiber matrix segment) may include both the inner layer 370 and the outer layer 380 to encapsulate the fiber matrix between the inner and outer layers. In one example, one or more longitudinal portions of the graft body that are free of the fiber matrix 130, or portions thereof, may be free of one of the inner layer 370 or the outer layer 380. In other words, the longitudinal portion of the graft body that is free of the fiber matrix 130 (e.g., the longitudinal portion positioned between adjacent transverse fiber matrix segments and/or the circumferential portion positioned between adjacent longitudinal fiber matrix segments) may include a single layer of nonwoven electrospun fibers (e.g., the layer 370 or the layer 380). In this manner, the thickness of the graft body may be reduced (e.g., along the portions that are free of the fiber matrix) compared to a graft body having inner and outer layers of graft material along substantially an entire length of the graft body. Such a reduced thickness may increase the flexibility of the graft body and/or reduce the profile of the graft body.

In any of the examples described herein, the thickness of the inner layer 370 and/or the outer layer 380 of nonwoven electrospun fibers may be manipulated by the electrospinning operator (e.g., by adjusting the speed of rotation and/or translation) for desired operational use. Additionally, or alternatively, the graft body 120 may be post-processed using manufacturing techniques (e.g., laser welding/marking, mechanical punching, etc.) to create varying porosity if desired. Additionally, or alternatively, the graft or covering material may be electrospun simultaneously with additional polymers, additives, or pharmacological agents to promote mechanical and/or chemical characteristics of the prosthesis. For example, the graft or covering material may be electrospun simultaneously with additional polymers such as PET (e.g., DACRON®, commercially available from Invista, Wichita, Kans.) or polyurethane (e.g., THORALON®, commercially available from Thoratec, Pleasanton, Calif.). In one example, the graft or covering material may include PET and polyurethane. Additionally, or alternatively, the graft or covering material may be electrospun simultaneously with additives or pharmacological agents such as, for example, lauric acid, levulinic acid, or polyethylene glycol (e.g., having a molecular weight of about 300, about 600, or any other suitable molecular weight). Electrospinning the graft or covering material with other materials may affect the mechanical properties (e.g., flexibility or strength) of the graft or covering material. Additionally, or alternatively, electrospinning the graft or covering material with other materials may affect the frictional properties and/or enable a reduced profile of the graft or covering material.

A covering formed by electrospinning as described herein may include a plurality of nonwoven fibers. In other words, the electrospun fibers may be configured as a mesh of fibers as opposed to a patterned weave or knit of fibers. The electrospun fibers may be nanofibers having a diameter of less than about 1,000 nm. Additionally, or alternatively, the electrospun covering may be substantially seamless. In other words, the covering may be substantially free of seams which may be formed, for example, by stitching together or otherwise attaching adjacent edges of one or more sheets of graft material.

In other examples, a graft body including a fiber matrix and/or a support structure at least partially encapsulated therein may be formed using any other suitable method including, for example, dip coating, spray coating, and melt-spinning. For example, an inner layer of graft material may be deposited on the outer surface of a mandrel by dipping the mandrel into a volume of liquid graft material. The liquid graft material on the outer surface of the mandrel may be dried or cured to form the inner layer of graft material on the mandrel. A fiber matrix may be placed over the inner layer of graft material formed on the mandrel. The mandrel with the inner layer of graft material and the fiber matrix positioned thereon may be dipped into the volume of liquid graft material to deposit an outer layer of graft material over the inner layer of graft material and/or the fiber matrix. In this manner, the fiber matrix may be at least partially encapsulated between the two layers of graft material.

Forming the graft body by electrospinning may enable a prosthesis having a reduced profile. For example, the thickness of a portion of the graft body (e.g., a portion of the graft body positioned longitudinally and/or circumferentially between adjacent fiber matrix segments) may have a thickness of less than about 70 µm, preferably less than about 25 µm. Additionally, or alternatively, a portion of the graft body including the fiber matrix may have a thickness of less than about 120 µm. A graft body with a reduced thickness may enable a prosthesis having a reduced profile. In other words, reducing the thickness of the graft body may enable reduction of the profile (e.g., the thickness or the diameter) of the prosthesis. Such a low-profile prosthesis may be delivered using a sheath having a reduced profile relative to conventional introducer sheaths. This may aid in advancing the sheath within a body vessel to the delivery site within the patient's anatomy. Additionally, or alternatively, providing a plurality of fiber matrix segments spaced from one another longitudinally along the graft body (e.g., a plurality of transverse fiber matrix segments) and/or circumferentially around the graft body (e.g., a plurality of longitudinal fiber matrix segments) may enable strengthening or reinforcing of portions of the graft body while maintaining a reduced profile (e.g., along portions of the graft body between transverse and/or longitudinal fiber matrix segments).

Additionally, or alternatively, providing a plurality of transverse fiber matrix segments spaced from one another longitudinally along the graft body may enable a prosthesis having increased flexibility compared to a prosthesis including a transverse fiber matrix extending along substantially the entire length thereof. For example, portions of the graft body that are free of the transverse fiber matrix (e.g., portions of the graft body between transverse fiber matrix segments) may have increased flexibility compared to portions of the graft body including the transverse fiber matrix segments. The graft body may be capable of flexing or bending to a greater degree at the portions having increased flexibility. Increased flexibility may enable increased maneuverability to deliver the prosthesis through tortuous anatomy. The longitudinal length of a transverse fiber matrix segment and/or the spacing between adjacent transverse fiber matrix segments may depend on factors such as, for example, the length of the prosthesis, the number of stent points or apices, or any other suitable factor. In one example, the spacing between adjacent transverse fiber matrix segments may be greater than or equal to the longitudinal length of a ring structure of the support structure (e.g., a Z-stent or other ring structure).

Additionally, or alternatively, encapsulating the fiber matrix within the covering of the graft body may reduce the porosity of at least a portion of the graft body. For example, a nanofiber construct (e.g., a covering of nonwoven electrospun fibers) over a fiber matrix (e.g., a woven PET fabric) may have a reduced porosity compared to the nanofiber construct without the fiber matrix. Such reduced porosity may reduce the potential for endoleaks.

Solutions for use in the electrospinning process of the present disclosure may include any suitable liquids containing materials to be electrospun (e.g., any of the graft materials described above). For example, solutions may include, but are not limited to, suspensions, emulsions, melts, and hydrated gels containing the materials, substances, or compounds to be electrospun. Solutions also may include solvents or other liquids or carrier molecules. Solutions may include, for example, any of the materials described in U.S. Pat. No. 7,799,261 to Orr et al., which is incorporated herein by reference. In one example, the solution 330 may include a PET such as, for example a DACRON® leg-fabric commercially available from Invista, Wichita, Kans. The solution 330 may include a polymer solution of PET in approximately 50:50 trifluoroacetic acid (TFA) and dichloromethane (DCM or methylene chloride) at a predetermined concentration, typically between about 0.1 g/mL and about 0.17 g/mL solvent.

Additionally, or alternatively, solutions may include one or more bioactive agents. A therapeutically effective amount of a bioactive agent may be incorporated into the graft material produced by the electrospinning process for implantation within a patient. The bioactive agent may be selected to perform a desired function upon implantation. For example, the bioactive agent may be selected to treat indications such as atherosclerosis, renal dialysis fistulae stenosis, or vascular graft stenosis. A graft material including a bioactive agent may be useful when performing procedures such as coronary artery angioplasty, renal artery angioplasty, or carotid artery surgery. Also for example, a bioactive agent such as a growth factor may be selected to promote ingrowth of tissue from the interior wall of a body vessel. An anti-angiogenic or antineoplastic bioactive agent such as paclitaxel, sirolimus, or a rapamycin analog, or a metalloproteinase inhibitor such as batimastat may be included to mitigate or prevent undesired conditions in the vessel wall, such as restenosis. Many other types of bioactive agents also may be included in the solution.

Although the electrospinning process has been described in relation to applying a graft material to a mandrel to form a covering, this disclosure is not so limited. The electrospinning process described above may be used to apply any type of coating to any type of medical device. For example, the electrospinning process may be used to apply a coating of a therapeutic agent to a stent or a covered stent (e.g., a stent graft).

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An expandable endoluminal prosthesis comprising:
   a graft body and a support structure attached to the graft body, the graft body comprising:
   a tubular body of nonwoven electrospun fibers disposed about a longitudinal axis, wherein the tubular body comprises an inner layer of nonwoven electrospun fibers and an outer layer of nonwoven electrospun fibers;
   a first fiber matrix comprising a plurality of discrete circumferentially wound filaments attached to the tubular body and extending circumferentially around the tubular body; and
   a second fiber matrix comprising a plurality of discrete longitudinally extending filaments attached to the tubular body and extending in a longitudinally along the tubular body
   wherein each of the first fiber matrix and the second fiber matrix are disposed along an inner surface of the outer layer of the nonwoven electrospun fibers such that the first fiber matrix and the second fiber matrix are encapsulated between the inner layer and the outer layer of nonwoven electrospun fiber.

2. The prosthesis of claim 1, wherein each of the first fiber matrix and the second fiber matrix comprises a filamentary member.

3. The prosthesis of claim 1, wherein the support structure is at least partially encapsulated between the inner layer and the outer layer.

4. The prosthesis of claim 3, wherein the support structure comprises a plurality of support structures spaced from one another along a length of the graft body, and at least one of the plurality of support structures is encapsulated between the inner layer and the outer layer.

5. The prosthesis of claim 1, wherein the first fiber matrix is longitudinally shorter than the graft body, a longitudinal portion of the graft body comprising the first fiber matrix comprises an attachment site, and the support structure is attached to the first fiber matrix at the attachment site to attach the support structure to the graft body.

6. The prosthesis of claim 5, wherein the first fiber matrix comprises a color that is different than a color of the tubular body to aid in identification of the attachment site.

7. The prosthesis of claim 1, wherein the first fiber matrix comprises a plurality of turns extending angularly around the longitudinal axis, and the second matrix extends less than about 360 degrees angularly around the longitudinal axis.

8. The prosthesis of claim 1, wherein the first fiber matrix and the second fiber matrix are formed from two or more discrete filamentary members.

9. An expandable endoluminal prosthesis comprising:
a graft body and a support structure attached to the graft body, the graft body comprising:
 a tubular body of nonwoven electrospun fibers disposed about a longitudinal axis, wherein the tubular body comprises an inner layer of nonwoven electrospun fibers and an outer layer of nonwoven electrospun fibers;
 a first fiber matrix attached to the tubular body and having fibers that extend circumferentially around the tubular body; and
 a second fiber matrix attached to the tubular body and having fibers that extend in a longitudinally along the tubular body,
wherein each of the first fiber matrix and the second fiber matrix are disposed along an inner surface of the outer layer of the nonwoven electrospun fibers such that the first fiber matrix and the second fiber matrix are encapsulated between the inner layer and the outer layer of nonwoven electrospun fibers,
wherein the first fiber matrix is longitudinally shorter than the graft body, a longitudinal portion of the graft body comprising the first fiber matrix comprises an attachment site, and the support structure is attached to the first fiber matrix at the attachment site to attach the support structure to the graft body, and
wherein the attachment site comprises a suture zone, and the support structure is sutured to the first fiber matrix to attach the support structure to the graft body.

10. An expandable endoluminal prosthesis comprising:
a graft body and a support structure attached to the graft body, the graft body comprising:
 a tubular body of nonwoven electrospun fibers disposed about a longitudinal axis, wherein the tubular body comprises an inner layer of nonwoven electrospun fibers and an outer layer of nonwoven electrospun fibers;
 a first fiber matrix attached to the tubular body and having fibers that extend circumferentially around the tubular body; and
 a second fiber matrix attached to the tubular body and having fibers that extend in a longitudinally along the tubular body,
wherein each of the first fiber matrix and the second fiber matrix are disposed along an inner surface of the outer layer of the nonwoven electrospun fibers such that the first fiber matrix and the second fiber matrix are encapsulated between the inner layer and the outer layer of nonwoven electrospun fibers, and
wherein at least one of the first fiber matrix and the second fiber matrix comprises a loop point comprising a loop of filamentary material extending away from the tubular body.

11. The prosthesis of claim 10, wherein the support structure is sutured to the loop point to attach the support structure to the graft body.

12. The prosthesis of claim 10, wherein a portion of the support structure is received within the loop point to attach the support structure to the graft body.

13. An expandable endoluminal prosthesis comprising:
a graft body and an expandable support structure attached to the graft body, the graft body comprising:
 a tubular body of nonwoven electrospun fibers disposed about a longitudinal axis, wherein the tubular body comprises an inner layer of nonwoven electrospun fibers and an outer layer of nonwoven electrospun fibers;
 a transverse fiber matrix comprising a plurality of discrete circumferentially wound filaments at least partially encapsulated within the tubular body and having fibers extending around a circumference of the tubular body; and
 a longitudinal fiber matrix comprising a plurality of discrete longitudinally extending filaments at least partially encapsulated within the tubular body and having fibers extending primarily longitudinally along the tubular body;
wherein the support structure is attached to at least one of the transverse fiber matrix and the longitudinal fiber matrix to attach the support structure to the graft body, and
wherein each of the transverse fiber matrix, the longitudinal fiber matrix, and the support structure are disposed along an inner surface of the outer layer of nonwoven electrospun fibers such that the transverse fiber matrix, the longitudinal fiber matrix, and the support structure are encapsulated between the inner layer and the outer layer of nonwoven electrospun fibers.

14. The prosthesis of claim 13, wherein the transverse fiber matrix is longitudinally shorter than the graft body.

15. The prosthesis of claim 14, wherein the transverse fiber matrix comprises a plurality of transverse fiber matrices spaced from one another along a length of the graft body.

16. The prosthesis of claim 13, wherein the longitudinal fiber matrix comprises a plurality of longitudinal fiber matrices spaced from one another around a circumference of the graft body.

17. A method for preparing an endoluminal prosthesis of claim 1, the method comprising:

providing an electrospinning apparatus comprising an orifice and a mandrel;

generating an electric potential between the orifice and the mandrel;

forming a first layer of nonwoven fibers on an outer surface of the mandrel by electrospinning a solution from the orifice onto the outer surface of the mandrel;

positioning a first fiber matrix comprising a plurality of discrete filaments over the first layer of fibers, the first fiber matrix having fibers extending transverse to a longitudinal axis of the first layer of nonwoven fibers;

positioning a second fiber matrix comprising a plurality of discrete filaments over the first layer of fibers, the second fiber matrix having fibers extending in a longitudinal direction and substantially parallel to the longitudinal axis of the first layer of nonwoven fibers;

positioning an expandable support structure over the first layer of nonwoven fibers; and forming a second layer of nonwoven fibers over the first fiber matrix, the second fiber matrix, and the support structure by electrospinning the solution from the orifice, whereby each of the first fiber matrix, the second fiber matrix, and the support structure are disposed along an inner surface of the second layer of nonwoven fibers such that the first fiber matrix, the second fiber matrix, and the support structure are encapsulated within a covering formed by the first layer of nonwoven fibers and the second layer of nonwoven fibers.

* * * * *